US012697384B2

(12) United States Patent
Masuda et al.

(10) Patent No.: US 12,697,384 B2
(45) Date of Patent: Aug. 4, 2026

(54) MULTIPLE ANTIGENIC PEPTIDE AGAINST CORONA VIRUS AND IMMUNOSTIMULATING COMPOSITION CONTAINING THE SAME

(71) Applicants:RIKEN, Saitama (JP); ANIMAL ALLERGY CLINICAL LABORATORIES INC., Sagamihara (JP)

(72) Inventors: Kenichi Masuda, Saitama (JP); Takashi Saito, Saitama (JP)

(73) Assignees: RIKEN, Saitama (JP); ANIMAL ALLERGY CLINICAL LABORATORIES INC., Kanagawa (JP)

( * ) Notice: Subject to any disclaimer, the term of this patent is extended or adjusted under 35 U.S.C. 154(b) by 921 days.

(21) Appl. No.: 17/926,975

(22) PCT Filed: May 21, 2021

(86) PCT No.: PCT/JP2021/019458
§ 371 (c)(1),
(2) Date: Nov. 21, 2022

(87) PCT Pub. No.: WO2021/235553
PCT Pub. Date: Nov. 25, 2021

(65) Prior Publication Data
US 2023/0218742 A1     Jul. 13, 2023

(30) Foreign Application Priority Data
May 22, 2020     (JP) ................................. 2020-089340

(51) Int. Cl.
| | |
|---|---|
| *A61K 39/215* | (2006.01) |
| *A61P 31/14* | (2006.01) |
| *C07K 14/005* | (2006.01) |
| *A61K 39/00* | (2006.01) |

(52) U.S. Cl.
CPC ............ *A61K 39/215* (2013.01); *A61P 31/14* (2018.01); *C07K 14/005* (2013.01); *A61K 2039/505* (2013.01); *A61K 2039/575* (2013.01); *A61K 2039/645* (2013.01); *A61K 2039/70* (2013.01)

(58) Field of Classification Search
None
See application file for complete search history.

(56) References Cited

U.S. PATENT DOCUMENTS

| | | | | |
|---|---|---|---|---|
| 2006/0199176 A1 * | 9/2006 | Wang | .................. | C07K 14/005 435/456 |
| 2008/0213284 A1 | 9/2008 | Sing Chong et al. | | |
| 2009/0017069 A1 | 1/2009 | Akeefe et al. | | |

| | | | | |
|---|---|---|---|---|
| 2017/0158738 A1 | 6/2017 | Masuda et al. | | |
| 2019/0276495 A1 * | 9/2019 | Masuda | ............... | C07K 14/001 |
| 2019/0337989 A1 | 11/2019 | Masuda et al. | | |

FOREIGN PATENT DOCUMENTS

| | | | | |
|---|---|---|---|---|
| EP | 3 892 298 A1 | 10/2021 | | |
| WO | WO-2004/111081 A2 | 12/2004 | | |
| WO | WO-2015/190555 A1 | 12/2015 | | |
| WO | WO-2018062217 A1 * | 4/2018 | ............. | A61K 39/39 |
| WO | WO-2021/173879 A1 | 9/2021 | | |
| WO | WO-2021/201777 A1 | 10/2021 | | |

OTHER PUBLICATIONS

International Search Report dated Aug. 31, 2021 in PCT/JP2021/019458.
Poh et al., "Two linear epitopes on the SARS-CoV-2 spike protein that elicit neutralising antibodies in COVID-19 patients," Nature Communications, Jun. 1, 2020, 11(2806):1-7.
Robson, B., "COVID-19 Coronarivus spike protein analysis for synthetic vaccines, a peptidomimetic antagonist, and therapeutic drugs, and analysis of a proposed achilles' heel conserved region to minimize probability of escape mutations and drug resistance," Computers in Biology and Medicine, Apr. 11, 2020, 121:1-28.
Saravanan et al., "Detection of Infectious Bursal Disease Virus by Elisa Using an Antipeptide Antibody Raised Against VP3 Region," Acta Virologica, 2004, 48(1):39-45.
Poh et al., "Potent neutralizing antibodies in the sear of convalescent COVID-19 patients are directed against conserved linear epitopes on the SARS-CoV-2 spike protein," bioRxiv, Mar. 31, 2020, 1-11.
Robson, B., "Computers and viral diseases. Preliminary bioinformatics studies on the design of a synthetic vaccine and a preventative peptidomimetic antagonist against the SARS-CoV-2 (2019-nCOV, COVID-19) coronavirus," Computers in Biology and Medicine, Feb. 26, 2020, 119:1-19.
Rojo, Javier, "Dendritic Compounds as Immune Response Modulators. New Approaches for Vaccine Development," Anti-Infective Agents in Medicinal Chemistry, Jan. 1, 2009, 8(1):50-72.
Supplementary European Search Report dated Jun. 19, 2024 in EP 21808352.5.
Tang et al., "Coronavirus membrane fusion mechanism offers a potential target for antiviral development," Antiviral Research, Apr. 6, 2020, 178:1-16, 104792.
Wang et al., "Immunodominant SARS Coronavirus Epitopes in Humans Elicited both Enhancing and Neutralizing Effects on Infection in Non-human Primates," ACS Infectious Diseases, Mar. 30, 2016, 2(5):361-376.

(Continued)

*Primary Examiner* — Shanon A. Foley
*Assistant Examiner* — Myron G Hill
(74) *Attorney, Agent, or Firm* — Foley & Lardner LLP

(57) ABSTRACT

The present invention provides a vaccine against a coronavirus. According to the present invention, there is provided a peptide consisting of the amino acid sequence set forth in SEQ ID NO: 1 or a partial peptide of a coronavirus spike protein consisting of the amino acid sequence corresponding to the amino acid sequence of SEQ ID NO: 1 and a multiple antigen peptide containing a plurality of any of these peptides.

17 Claims, 18 Drawing Sheets

Specification includes a Sequence Listing.

(56)     References Cited

OTHER PUBLICATIONS

Francis et al., "Non-responsiveness to a foot-and-mouth disease virus peptide overcome by addition of foreign helper T-cell determinants," Nature, Nov. 12, 1987, 330(6144):168-170.

Lim et al., "Development of multi-epitope peptide-based vaccines against SARS-CoV-2," Biomedical Journal, Feb. 2021 (online Oct. 1, 2020), 44(1):18-30.

Oscherwitz et al., "Synthetic Peptide Vaccine Targeting a Cryptic Neutralizing Epitope in Domain 2 of Bacillus anthracis Protective Antigen," Infection and Immunity, Aug. 2009, 77(8):3380-3388.

Tam et al., "Vaccine engineering: Enhancement of immunogenicity of synthetic peptide vaccines related to hepatitis in chemically defined models consisting of T- and B-cell epitopes," Proc. Natl. Acad. Sci. USA, Dec. 1989, 86:9084-9088.

* cited by examiner

FIG. 1
Conventional vaccine

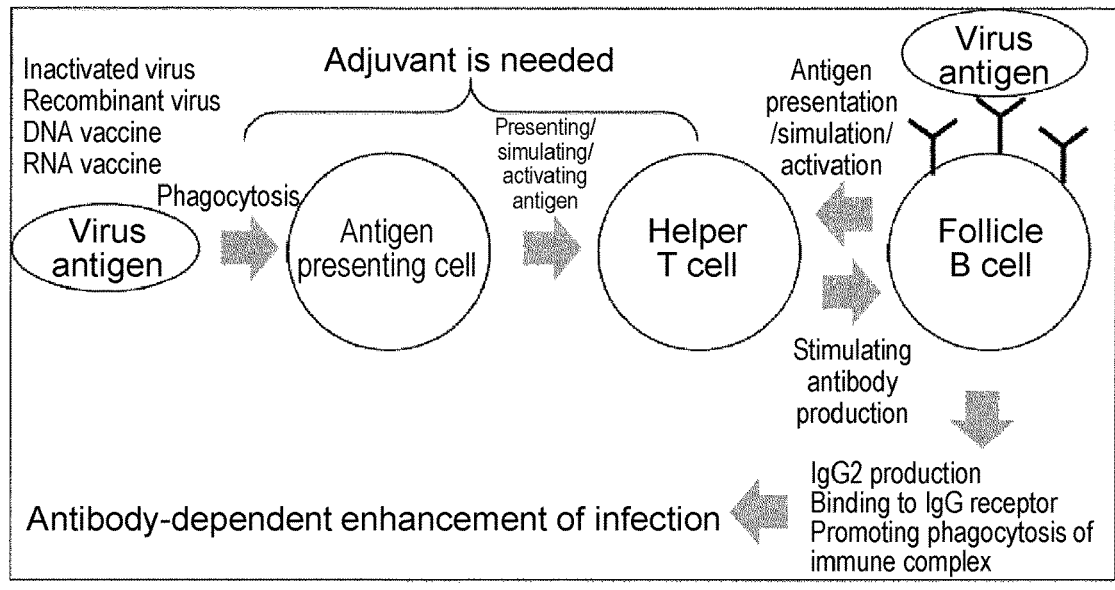

Inactivated virus
Recombinant virus
DNA vaccine
RNA vaccine

Adjuvant is needed

Phagocytosis

Virus antigen

Presenting/ simulating/ activating antigen

Antigen presentation /simulation/ activation

Virus antigen

Antigen presenting cell

Helper T cell

Follicle B cell

Stimulating antibody production

IgG2 production
Binding to IgG receptor
Promoting phagocytosis of immune complex Antibody-dependent enhancement of infection

FIG. 2
Coronavirus vaccine of the invention

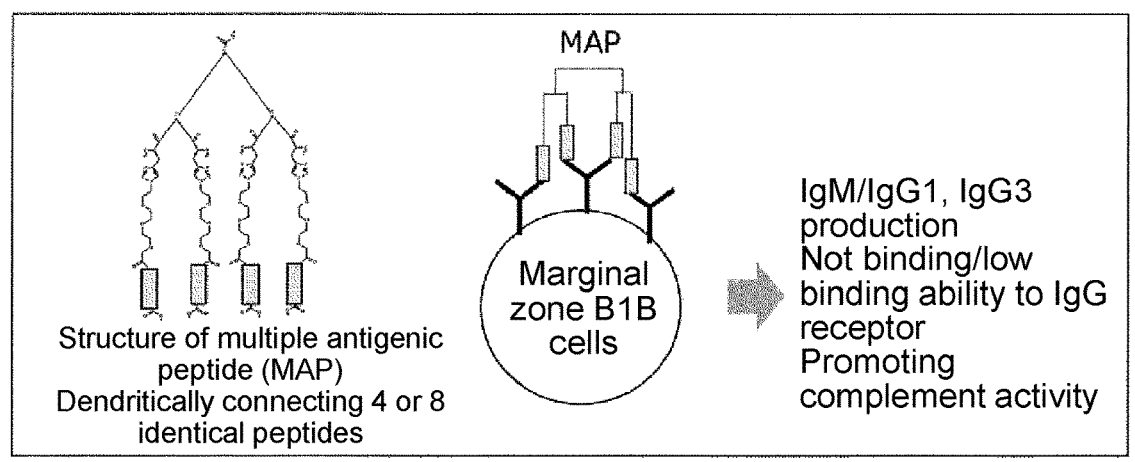

MAP

Structure of multiple antigenic peptide (MAP)
Dendritically connecting 4 or 8 identical peptides Marginal zone B1B cells IgM/IgG1, IgG3 production
Not binding/low binding ability to IgG receptor
Promoting complement activity

FIG. 3

```
SARS-CoV-2  -FA----------------QVKQIYKTPP----IKDFGGFNFSQILPD-PSKPSKR   819
FIPV        LFVSENALKLASVEAFNSTENLDPIYKEWPSIGGSWLGGL---KDILPSHNSKRKYG   965
SARS-CoV    -FA----------------QVKQMYKTPT----LKYFGGFNFSQILPD-PLKPTKR   801
             *.               :.,  :**       . :**: ,:***.   *    * **

SARS-CoV-2  TLADAGFI-KQYGDCLGDIAARDLICAQKFNGLTVLPPLLTDEMIAQYTSALL   878
FIPV        VTSGLGTVDEDYKRCTGGYDIADLVCAQYYNGIMVLPGVANADKMTMYTASLA   1025
SARS-CoV    TLADAGFM-KQYGECLGDINARDLICAQKFNGLTVLPPLLTDDMIAAYTAALV   860
            ****:**. :. * : ::* * *.    **:*** :**: ***  . .   :: **::*
```

FIG. 4
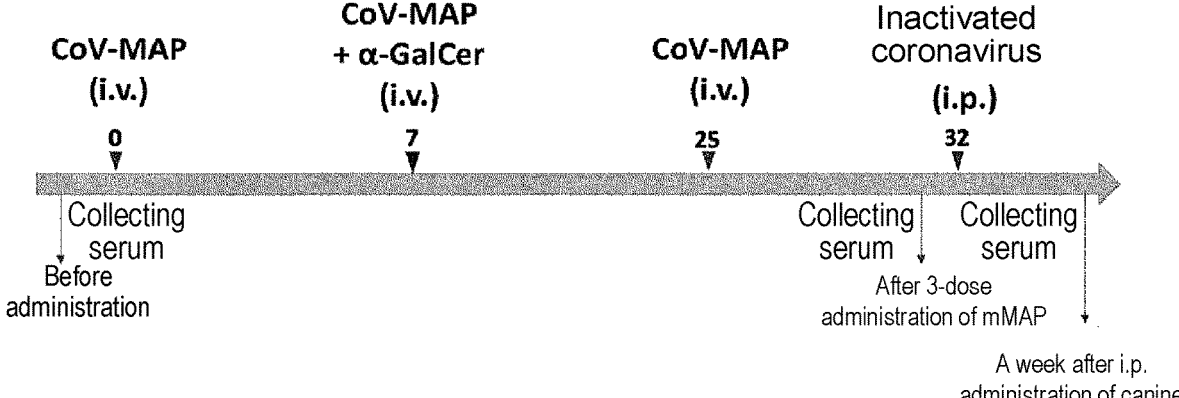
FIG. 5
Antibody titer of serum <u>IgM</u> against canine coronavirus
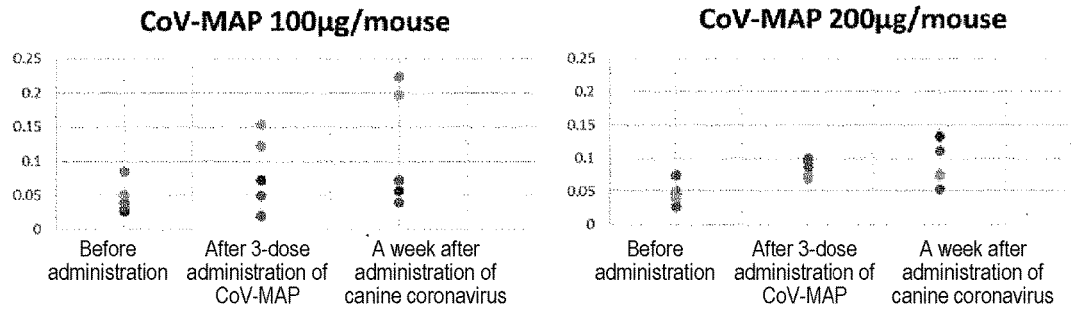
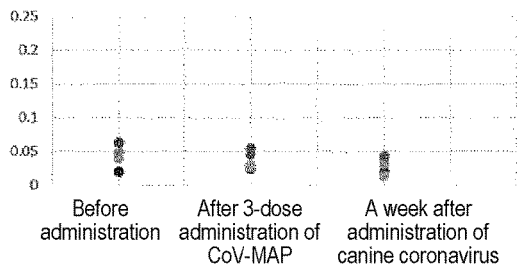

Against porcine epidemic diarrhea (PED) virus

IgG

IgM measurement

D-CoV-$\beta$-mMAP          D-form peptide immobilized

| CoV-mMAP (i.v.) | CoV-mMAP +α-GalCer (i.v.) | CoV-mMAP (i.v.) | Boost vaccination with canine coronavirus vaccine antigen (i.p.) |
|---|---|---|---|
| Cont-MAP (i.v.) | Cont-MAP +α-GalCer (i.v.) | Cont-MAP (i.v.) | Boost vaccination with canine coronavirus vaccine antigen (i.p.) |
| Day 0 | Day 7 | Day 25 | Day 32 |

MAP: 200 µg/mouse per administration
α-GalCer: 0.1 µg/mouse

Comparative general peptide vaccine : KLH-bound SAIEDLLFNKV+ alum i.p.

| Day 0 | Day 7 | Day 28 |
|---|---|---|

IgM against peptide (SAIEDLLFNKV)

IgM against canine coronavirus antigen

IgM against porcine epidemic diarrhea virus antigen

Change of IgM value relative to highly pathogenic coronavirus antibody

FIG. 14
Change of IgM by 4 valent CoV-mMap
IgM against peptide
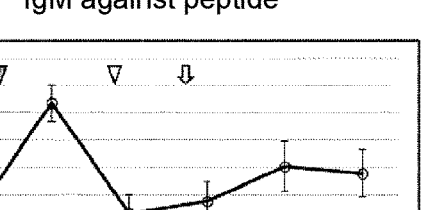
IgM against porcine coronavirus
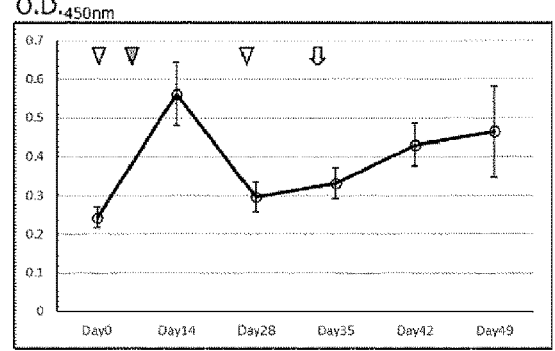
IgM against canine coronavirus
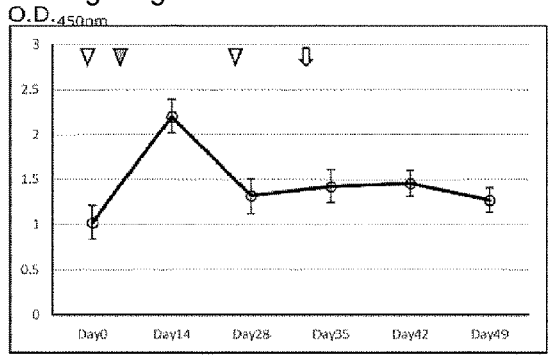
FIG. 15
No.2 D-form amino acid peptide MAP : SAIEDLLFNKV
IgM against peptide
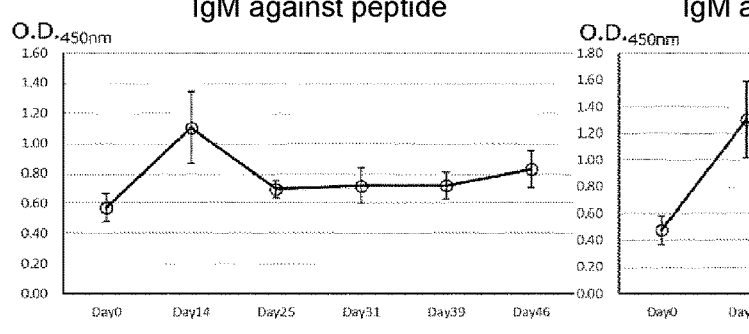
IgM against canine coronavirus
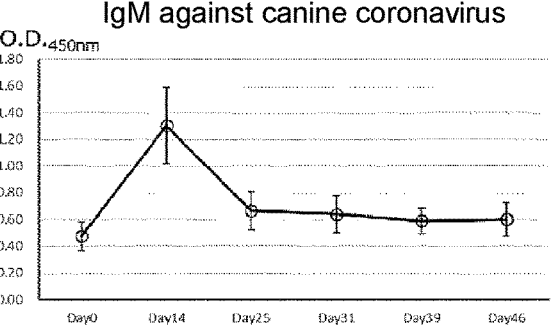
IgM against porcine coronavirus
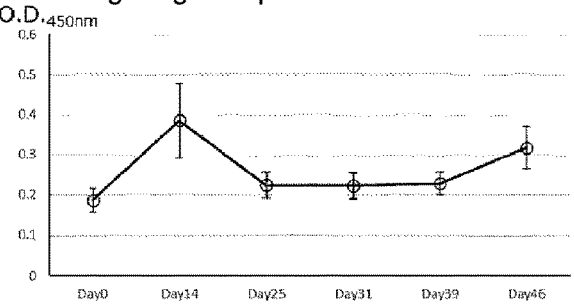

FIG. 16
No. 3 partial D-form MAP : SAIED*LLF*NKV
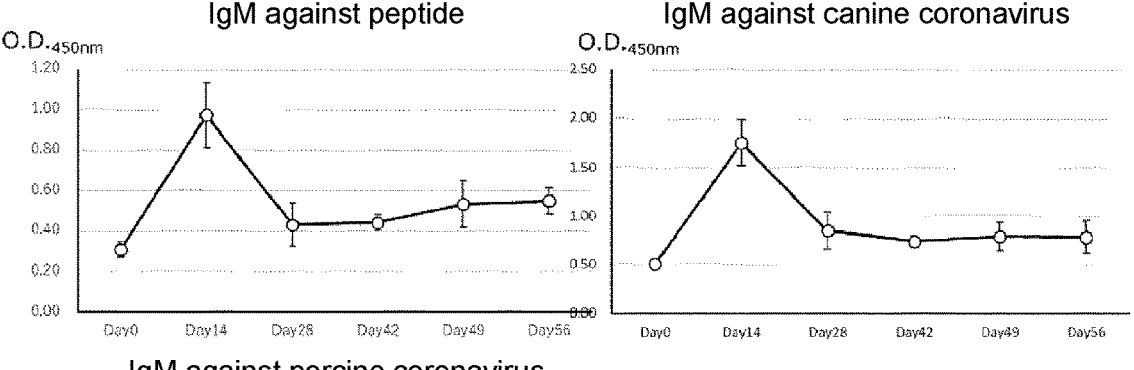
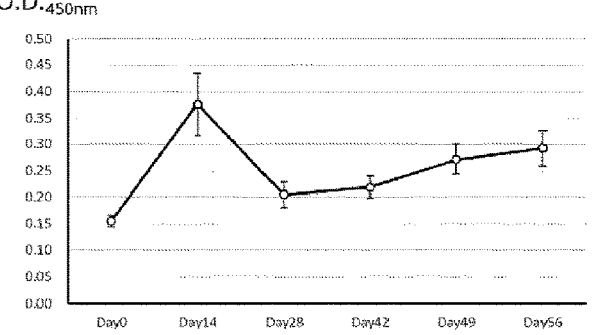
FIG. 17
No. 4 partial D-form MAP : *SAIED*LLF*NKV*
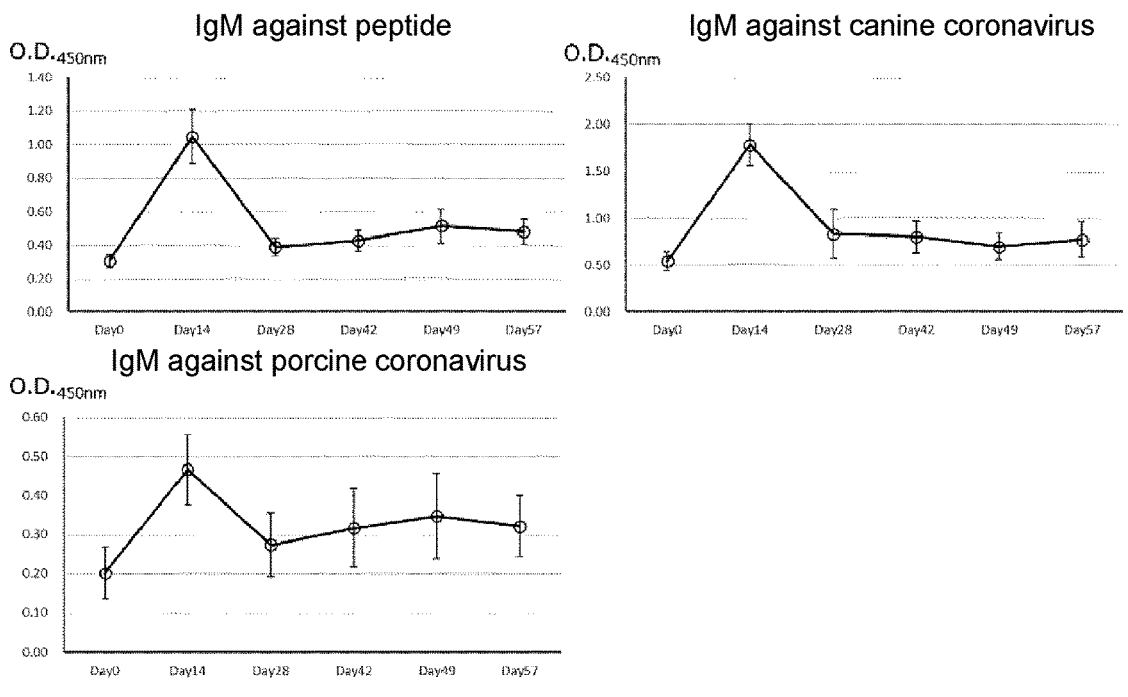

FIG. 18
No. 5 single amino acid substituted peptide MAP : SAIEDLLFDKV(N→D)
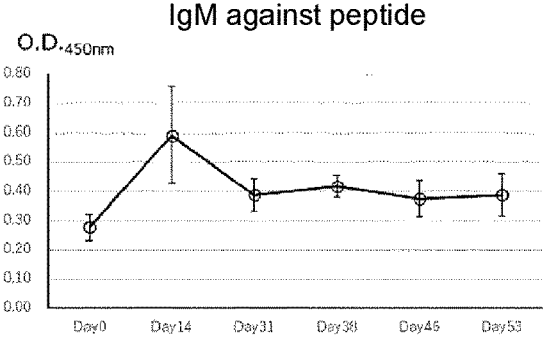
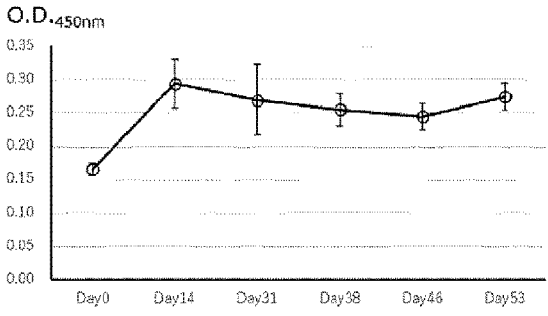
FIG. 19
No. 6 single amino acid substituted peptide MAP : SFIEDLLFNKV (A→F)
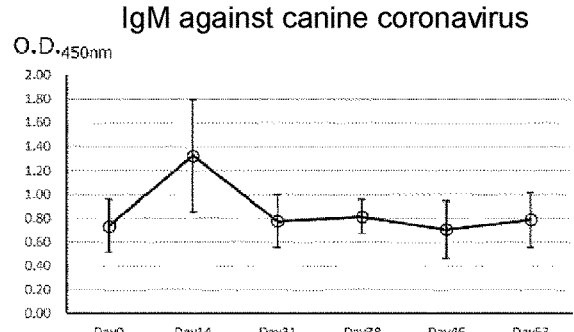
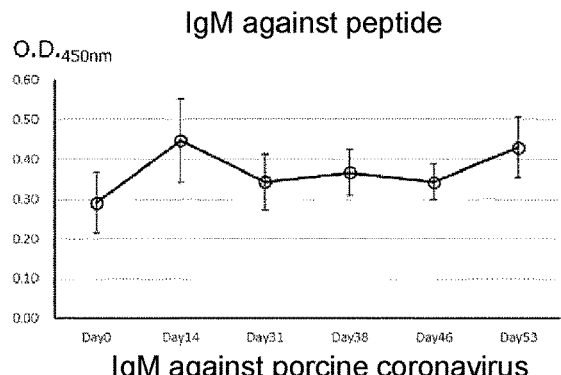

FIG. 20

Comparison of reactivity of various peptide MAPs having amino acid substitution Weekly change of IgM value ratio to Day 0 (regarded as 1) (wks)

Change of IgM value ratio to canine coronavirus          Change of IgM value ratio to porcine coronavirus

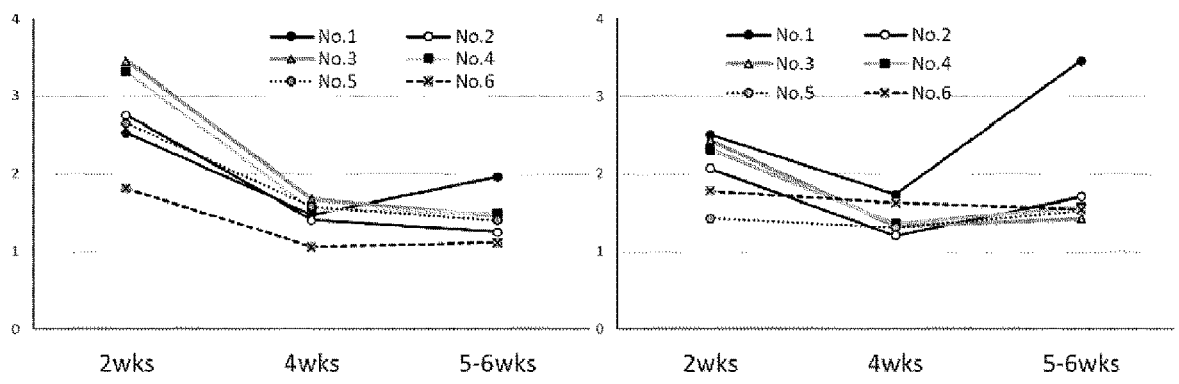

FIG. 21

Long-term maintenance of CoV-mMAP (No. 1) induced IgM (persistence of vaccine effect)

— Comparison of measurement-value ratio (Day 137/Day 0) —

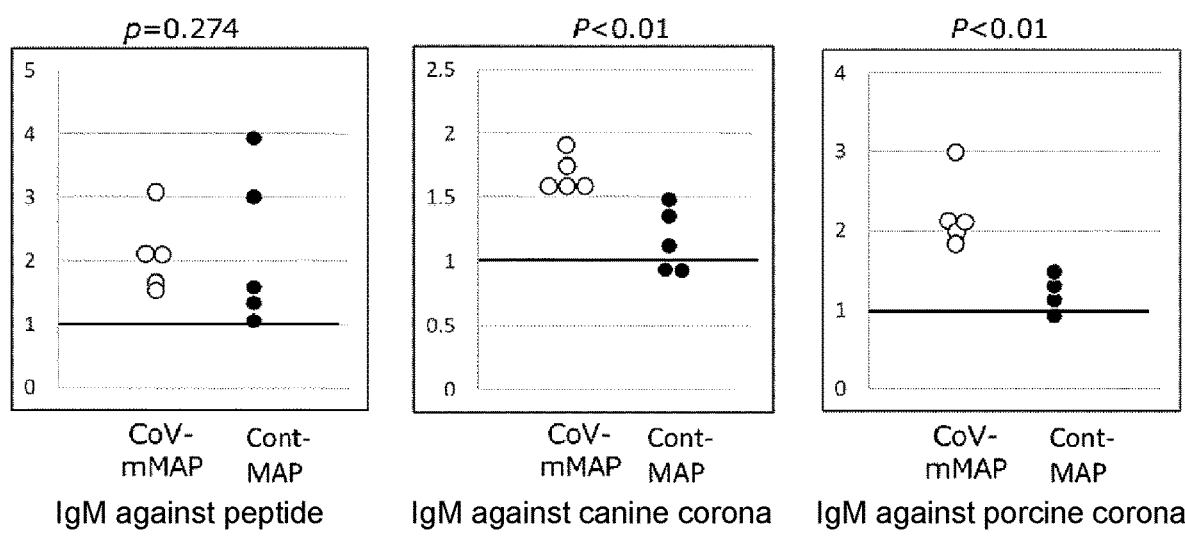

Long-term maintenance of CoV-mMAP induced IgM
(establishment of immunological memory)
ELISPOT method Number of peptide IgM production cells
(in $5 \times 10^5$ cells) in spleen on Day 133

Peptide-FLAG-BSA
+ serum of mice
immunized with
CoV-mMAP

Peptide-FLAG-BSA
+ non-treated
mouse serum
(negative control)

Peptide-FLAG-BSA
+ anti-FLAG
monoclonal
antibody-PE
(positive control)

IgG against various coronaviruses after pseudo-infection
(Day 25 after administration of canine coronavirus vaccine)

IgG against highly pathogenic coronavirus after pseudo-infection
(Day 25 after administration of canine coronavirus vaccine)

Comparison among IgG subclasses induced
by CoV-mMAP or KLH peptide
(Anti-peptide antibody)

Cause of ADE taken by macrophages

Vaccine administration and virus exposure using cat FIPV infection model

Change of fever in cat with FIP

SEQUENCE LISTING

<160> NUMBER OF SEQ ID NOS: 8

<210> SEQ ID NO 1
<211> LENGTH: 11

```
<212> TYPE: PRT
<213> ORGANISM: Artificial Sequence
<220> FEATURE:
<223> OTHER INFORMATION: SARS-CoV-2 antigen peptide

<400> SEQUENCE: 1

Ser Phe Ile Glu Asp Leu Leu Phe Asn Lys Val
1               5                   10

<210> SEQ ID NO 2
<211> LENGTH: 11
<212> TYPE: PRT
<213> ORGANISM: Artificial Sequence
<220> FEATURE:
<223> OTHER INFORMATION: FIPV antigen peptide

<400> SEQUENCE: 2

Ser Ala Ile Glu Asp Leu Leu Phe Asp Lys Val
1               5                   10

<210> SEQ ID NO 3
<211> LENGTH: 31
<212> TYPE: PRT
<213> ORGANISM: Artificial Sequence
<220> FEATURE:
<223> OTHER INFORMATION: SARS-CoV-2 antigen peptide L

<400> SEQUENCE: 3

Leu Pro Asp Pro Ser Lys Pro Ser Lys Arg Ser Phe Ile Glu Asp Leu
1               5                   10                  15

Leu Phe Asn Lys Val Thr Leu Ala Asp Ala Gly Phe Ile Lys Gln
            20                  25                  30

<210> SEQ ID NO 4
<211> LENGTH: 25
<212> TYPE: PRT
<213> ORGANISM: Artificial Sequence
<220> FEATURE:
<223> OTHER INFORMATION: SARS-CoV-2 antigen peptide embeded in beta-
      sheet peptide

<400> SEQUENCE: 4

Asp Arg Ser Phe Ile Glu Asp Leu Leu Phe Asn Lys Val Gly Lys Gly
1               5                   10                  15

Ser Ile Asp Thr Ser Ala Lys Phe Ser
            20                  25

<210> SEQ ID NO 5
<211> LENGTH: 25
<212> TYPE: PRT
<213> ORGANISM: Artificial Sequence
<220> FEATURE:
<223> OTHER INFORMATION: Influenza antigen peptide

<400> SEQUENCE: 5

Asp Gly Trp Tyr Gly Phe Arg His Gln Asn Ser Glu Gly Thr Gly Gln
1               5                   10                  15

Ala Ala Asp Leu Lys Ser Thr Gln Ala
            20                  25
```

US 12,697,384 B2

39                                                          40

-continued

```
<210> SEQ ID NO 6
<211> LENGTH: 11
<212> TYPE: PRT
<213> ORGANISM: Artificial Sequence
<220> FEATURE:
<223> OTHER INFORMATION: PEDV antigen peptide

<400> SEQUENCE: 6

Ser Val Ile Glu Asp Leu Leu Phe Asn Lys Val
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Antigen peptide
<220> FEATURE:
<221> NAME/KEY: MISC_FEATURE
<222> LOCATION: (2)..(2)
<223> OTHER INFORMATION: X = V, A, or F
<220> FEATURE:
<221> NAME/KEY: MISC_FEATURE
<222> LOCATION: (9)..(9)
<223> OTHER INFORMATION: X = D or N

<400> SEQUENCE: 7

Ser Xaa Ile Glu Asp Leu Leu Phe Xaa Lys Val
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Peptide antigen

<400> SEQUENCE: 8

Ser Ala Ile Glu Asp Leu Leu Phe Asn Lys Val
1               5                   10
```

1

MULTIPLE ANTIGENIC PEPTIDE AGAINST CORONA VIRUS AND IMMUNOSTIMULATING COMPOSITION CONTAINING THE SAME

CROSS-REFERENCE TO RELATED APPLICATIONS

This application is the U.S. National Stage of PCT/JP2021/019458, filed May 21, 2021, which claims priority to JP 2020-089340, filed May 22, 2020.

The instant application contains a Sequence Listing that has been submitted in ASCII format via EFS-WEB and is hereby incorporated by reference in its entirety. Said ASCII copy, created on Nov. 21, 2022, is named sequence.txt and is 2,581 bytes.

TECHNICAL FIELD

The present invention relates to a multiple antigen peptide against a coronavirus and an immunostimulatory composition containing the peptide, and particularly, to a vaccine against a coronavirus.

BACKGROUND ART

It has long been known that antibody elevation can be induced by a multiple antigen peptide (MAP) in vivo without involving T cells (Non Patent Literature 1). It has been shown that an autoantibody (anti-IgE antibody), which is not easily induced in vivo, can be induced by a MAP (Patent Literature 1). Patent Literature 2 discloses that a general virus MAP is prepared by using a peptide site of virus causing Ebola hemorrhagic fever in the aforementioned manner and a mouse is immunized with the general virus MAP to induce a desired antibody in serum. Similarly, Patent literature 3 discloses that a general virus MAP is prepared by using a partial peptide of influenza-virus hemagglutinin, and a mouse is immunized with the general virus MAP to induce a desired antibody in serum.

CITATION LIST

Patent Literatures

Patent Literature 1: US2017-0158738A
Patent Literature 2: US2019-0276495A
Patent Literature 3: US2019-0337989A

Non Patent Literature

Non Patent Literature 1: Saravanan, P., et. al., Acta Virol., (48) 39-45, 2004

SUMMARY OF INVENTION

The present invention provides a multiple antigen peptide against a coronavirus and an immunostimulatory composition containing the peptide, and particularly, a vaccine against a coronavirus. According to the present invention, there are provided a multiple antigen peptide, which contains a peptide consisting of an amino acid sequence set forth in SEQ ID NO: 1, or a partial peptide of a coronavirus spike protein consisting of the amino acid sequence corresponding to the amino acid sequence of SEQ ID NO: 1 (a peptide consisting of the amino acid sequence of a coronavirus spike protein corresponding to an amino acid sequence of 11 to 21 consecutive amino acids in length containing the amino acid sequence set forth in SEQ ID NO: 1), and a plurality of any one of the peptides.

The present inventors have found that a multiple antigen peptide (MAP), which has a peptide consisting of the amino acid sequence set forth in SEQ ID NO: 1, or a partial peptide of a coronavirus spike protein consisting of the amino acid sequence corresponding to the amino acid sequence of SEQ ID NO: 1 is used to induce antigen-specific IgM, allowing the antigen-specific IgM to be maintained in blood for a long period of time. They have also revealed that the MAP induces formation of immunological memory. They have further found that the MAP can directly stimulate antibody production from marginal zone B cells and B1B cells to induce antibody production in T cell-independent manner. The present inventors have found that the multiple antigen peptide induces production of antibodies against a wide variety of coronaviruses. Furthermore, the present inventors have conducted experiments of infecting cats with a highly pathogenic coronavirus, feline infectious peritonitis virus (FIPV), and have found that administration of the multiple antigen peptide of the present invention early after onset (for example, by three days after confirmation of high fever, which is an early symptom in most cases) is effective in preventing aggravation of infection and recovery from the infection.

The present invention (application) provides the following inventions.

[1] A peptide consisting of a part of an amino acid sequence set forth in SEQ ID NO: 3, which is an amino acid sequence having 11 to 21 consecutive amino acids in length containing an amino acid sequence set forth in SEQ ID NO: 1, or a partial peptide of a coronavirus spike protein consisting of an amino acid sequence corresponding to the amino acid sequence having 11 to 21 consecutive amino acids in length (or a peptide consisting of the amino acid sequence of the coronavirus spike protein corresponding to an amino acid sequence having 11 to 21 consecutive amino acids in length).

[2] The peptide according to [1], which is a peptide consisting of the amino acid sequence set forth in SEQ ID NO: 1, or a partial peptide of a coronavirus spike protein consisting of an amino acid sequence corresponding to the amino acid sequence of SEQ ID NO: 1 (or a peptide consisting of the amino acid sequence of the coronavirus spike protein corresponding to an amino acid sequence having 11 to 21 consecutive amino acids in length).

[3] The peptide according to [2], wherein the amino acid sequence corresponding to SEQ ID NO: 1 has any one of addition, insertion, substitution and deletion of one base in the amino acid sequence set forth in SEQ ID NO: 1.

[4] The peptide according to [2] or [3], wherein the amino acid sequence corresponding to SEQ ID NO: 1 is a peptide consisting of an amino acid sequence set forth in SEQ ID NO: 2.

[5] A multiple antigen peptide containing the peptide according to any one of [1] to [4].

[6] The multiple antigen peptide according to [5], containing 4 or more peptides according to any one of [1] to [4], or 4 or more peptides having the amino acid sequence set forth in SEQ ID NO: 7

[7] A vaccine against a coronavirus, containing the multiple antigen peptide according to [6].

[8] The vaccine according to [7] containing no adjuvant.

[9] The vaccine according to [6] or [7] to be used in combination with α-galactosylceramide and no other adjuvants.

[10] The vaccine according to any one of [7] to [9], wherein the coronavirus is SARS-CoV-2 or a SARS-CoV-2 mutant.

[11] A method for activating immunity against a coronavirus in a subject that needs the activation, comprising administering an effective amount of the multiple antigen peptide according to [5] or [6] to the subject.

[1A] A peptide consisting of an amino acid sequence having 11 to 21 consecutive amino acids in length containing an amino acid sequence set forth in SEQ ID NO: 1 or a partial peptide of a coronavirus spike protein consisting of an amino acid sequence corresponding to the amino acid sequence of 11 to 21 consecutive amino acids in length (or a peptide consisting of the amino acid sequence of the coronavirus spike protein corresponding to an amino acid sequence of 11 to 21 consecutive amino acids in length).

[2A] The peptide according to [1A], which is a peptide consisting of the amino acid sequence set forth in SEQ ID NO: 1 or a partial peptide of a coronavirus spike protein consisting of the amino acid sequence corresponding to the amino acid sequence of SEQ ID NO: 1 (or a peptide consisting of the amino acid sequence of the coronavirus spike protein corresponding to an amino acid sequence having 11 to 21 consecutive amino acids in length).

[3A] The peptide according to [2A], wherein the amino acid sequence corresponding to SEQ ID NO: 1 has any one of addition, insertion, substitution and deletion of one base in the amino acid sequence set forth in SEQ ID NO: 1.

[4A] The peptide according to [2A] or [3A], wherein the amino acid sequence corresponding to SEQ ID NO: 1 is a peptide consisting of an amino acid sequence set forth in SEQ ID NO: 2.

4 to [5A], or 4 or more peptides having an amino acid sequence set forth in SEQ ID NO: 7.

[8A] The multiple antigen peptide according to [6A] or [7A], containing a dendritic polymer backbone and a peptide, wherein the peptide is the peptide according to any one of claims 1 to 5 and is linked to a tail end of the dendritic polymer backbone.

[9A] The multiple antigen peptide according to [8A], wherein the dendritic polymer backbone and the peptide are linked via a linker to each other.

[10A] The multiple antigen peptide according to [8A] or [9A], wherein, in the dendritic polymer backbone, to each of 2 amino groups of a lysine residue, a lysine residue forming a first-generation branch is bound via a peptide bond; and to each of 4 amino groups of the lysine residues forming a first-generation branch thus formed, a peptide is linked with or without a linker.

[11A] The multiple antigen peptide according to [8A] or [9A], wherein, in the dendritic polymer backbone, to each of 2 amino groups of a lysine residue, a lysine residue forming a first-generation branch is bound via a peptide bond; to each of 4 amino groups of the lysine residues forming a first-generation branch, a lysine reside forming a second-generation branch is bound via a peptide bond; and to each of 5 or more, 6 or more, 7 or more or 8 or more amino groups of the lysine residues forming a second-generation branch thus formed, a peptide is linked with or without a linker.

[12A] The multiple antigen peptide according to any one of [6A] to [10A], having the following formula (VI):

(VI)

[5A] A part of the peptide according to [1A] or [2A], which is a part of an amino acid sequence set forth in SEQ ID NO: 3.

[6A] A multiple antigen peptide comprising the peptide according to any one of [1A] to [5A].

[7A] The multiple antigen peptide according to [6A], containing 4 or more peptides according to any one of [1A]

wherein R represents linker-peptide or -peptide; the peptide is the peptide according to any one of [1A] to [5A]; $R^2$ represents a hydrogen atom, an OH group, a substituted or unsubstituted lower alkyl group, an amino group, an amino acid (particularly, 3-aminopropanoic acid ($\beta$-alanine)), a halogen atom or a peptide; and the amino acid is linked to the above molecule via an amide bond.

[13A] A vaccine against a coronavirus, containing the multiple antigen peptide according to any one of [6A] to [12A].

[14A] The vaccine according to [13A], containing no adjuvants.

[15A] The vaccine according to [13A] or [14A] to be used in combination with α-galactosylceramide and not with any other adjuvants.

[16A] The vaccine according to any one of [13A] to [15A], wherein the coronavirus is SARS-CoV-2 or a mutant virus thereof.

[17A] The vaccine according to any one of [13A] to [15A], wherein the coronavirus is one or more coronaviruses selected from porcine epidemic diarrhea virus (PED), canine coronavirus and feline infectious peritonitis virus (FIPV).

[18A] A pharmaceutical composition containing the multiple antigen peptide according to any one of [6A] to [12A].

[19A] The pharmaceutical composition according to [18A], for use in activating immunity against a coronavirus in a subject.

[20A] The pharmaceutical composition according to [18A] or [19], for use in inducing antigen-specific immunity against a coronavirus in a subject.

[21A] The pharmaceutical composition according to any one of [18A] to [20A], for use in inducing an antigen-specific IgM antibody against a coronavirus in a subject.

[22A] The pharmaceutical composition according to any one of [18A] to [21A], for use in inducing formation of immunological memory against a coronavirus in a subject.

[23A] The pharmaceutical composition according to any one of [18A] to [22A], for use in preventing and/or treating an infection disease with a coronavirus in a subject.

[24A] Use of the multiple antigen peptide according to any one of [6A] to [12A] in the manufacture of a medicament for use in activating immunity against a coronavirus in a subject.

[25A] Use of the multiple antigen peptide according to any one of [6A] to [12A] in the manufacture of a medicament for use in inducing antigen-specific immunity against a coronavirus in a subject.

[26A] Use of the multiple antigen peptide according to any one of [6A] to [12A] in the manufacture of a medicament for use in inducing an antigen-specific IgM antibody against a coronavirus in a subject.

[27A] Use of the multiple antigen peptide according to any one of [6A] to [12A] in the manufacture of a medicament for inducing formation of immunological memory against a coronavirus in a subject.

[28A] Use of the multiple antigen peptide according to any one of [6A] to [12A] in the manufacture of a medicament for preventing and/or treating an infection disease with a coronavirus in a subject.

[29A] A method for administering a peptide to a subject, comprising administering an effective amount of the pharmaceutical composition according to [18A] to the subject.

[30A] A method for activating immunity against a coronavirus in a subject, comprising administering an effective amount of the pharmaceutical composition according to [18A] to the subject.

[31A] A method for inducing antigen-specific immunity against a coronavirus in a subject, comprising administering an effective amount of the pharmaceutical composition according to [18A] to the subject.

[32A] A method for inducing an antigen-specific IgM antibody against a coronavirus in a subject, comprising administering an effective amount of the pharmaceutical composition according to [18A] to the subject.

[33A] A method for inducing formation of immunological memory against a coronavirus in a subject, containing administering an effective amount of the pharmaceutical composition according to [18A] to the subject.

[34A] A method for preventing and/or treating an infection disease with a coronavirus in a subject, comprising administering an effective amount of the pharmaceutical composition according to [18A] to the subject.

[35A] The pharmaceutical composition according to any one of [19] to [23], wherein the subject is a subject not infected with a coronavirus.

[36A] The pharmaceutical composition according to any one of [19] to [23], wherein the subject is a subject infected with a coronavirus.

[37A] The pharmaceutical composition according to any one of [19] to [23], wherein the subject is a subject that developed an infection disease with a coronavirus.

[38A] The use according to any one of [24] to [28], wherein the subject is a subject not infected with a coronavirus.

[39A] The use according to any one of [24] to [28], wherein the subject is a subject infected with a coronavirus.

[40A] The use according to any one of [24] to [28], wherein the subject is a subject that developed an infection disease with a coronavirus.

[41A] The method according to any one of [29] to [34], wherein the subject is a subject not infected with a coronavirus.

[42A] The method according to any one of [29] to [34], wherein the subject is a subject infected with a coronavirus.

[43A] The method according to any one of [29] to [34], wherein the subject is a subject that developed an infection disease with a coronavirus.

[44A] The pharmaceutical composition according to any one of [19] to [23], wherein the coronavirus is one or more coronaviruses selected from porcine epidemic diarrhea virus (PED), canine coronavirus and feline infectious peritonitis virus (FIPV).

[45A] The use according to any one of [24] to [28], wherein the coronavirus is one or more coronaviruses selected from porcine epidemic diarrhea virus (PED), canine coronavirus and feline infectious peritonitis virus (FIPV).

[46A] The method according to any one of [29] to [34], wherein coronavirus is one or more coronaviruses selected from porcine epidemic diarrhea virus (PED), canine coronavirus and feline infectious peritonitis virus (FIPV).

The multiple antigen peptide of the present invention is advantageous in inducing production of an antibody against a coronavirus. Since immunological memory is formed after administration of the multiple antigen peptide of the present invention, the multiple antigen peptide of the present invention is advantageous in further enhancing antibody production by viral infection. The multiple antigen peptide of the present invention stimulates not helper T cells and follicle B cells but marginal zone B cells and B1B cells in a T cell-independent manner to produce an antibody. For the reason, it is considered that the produced antibody can prevent antibody-dependent enhancement of infection. In this respect, the multiple antigen peptide of the present invention is advantageous. The multiple antigen peptide of the present invention is further advantageous in being effective for a highly pathogenic coronavirus. The multiple antigen peptide of the present invention is advantageous in being effective as a preventive treatment as well as a therapeutic treatment.

BRIEF DESCRIPTION OF DRAWINGS

FIG. 1 illustrates how to stimulate the immune system by a conventional virus vaccine (more specifically, inactivated virus vaccine, recombinant protein vaccine, DNA vaccine and RNA vaccine). Conventional vaccines require an adjuvant for stimulating the immune system and induce, in combination with an adjuvant, phagocytosis of the vaccine by macrophages, presentation of an antigen to helper T cells and activation of helper T cells. The activated helper T cells stimulate follicle B cells expressing a B cell receptor having an affinity for a virus antigen to produce IgG from the follicle B cells, in a T cell dependent manner. IgM produced by follicle B cells temporarily increases in blood concentration but disappears in about 2 weeks; whereas, IgG is present for a long period of time in blood and subtypes thereof which binds to the IgG receptor on macrophages are mainly present. Because of this, antibody-dependent enhancement of infection (ADE) is caused by IgG produced by follicle B cells at the time of viral infection, with the result that viral infection is promoted, causing serious symptoms.

FIG. 2 shows a schematic view of a molecular structure of the coronavirus vaccine of the present invention (more specifically, multiple antigen peptide), and illustrates that the multiple antigen peptide stimulates marginal zone B cells and B1B cells. When the marginal zone B cells and B1B cells are stimulated by the multiple antigen peptide, they produce IgM and IgG without involving helper T cells. As a result, IgM produced in a T cell-independent manner is present for a long period of time in blood and IgG subtypes which binds to an IgG receptor are not contained. Therefore, it is suggested that the coronavirus vaccine of the present invention, which allows not follicle B cells but marginal zone B cells and B1B cells to produce IgM and IgG, provides long-term antiviral defense and no antibody-dependent enhancement of infection.

FIG. 3 shows a part of alignment of amino acid sequences of spike proteins of a coronavirus of SARS (SARS-CoV) spread in 2003, feline infectious peritonitis virus (FIPV) and a coronavirus of SARS (SARS-CoV-2) spread in 2019. The peptide of the present invention was designed for the shaded area.

FIG. 4 shows an experimental scheme for administration of the multiple antigen peptide of the present invention (CoV-MAP) and administration of an inactivated virus simulating the following infection.

FIG. 5 shows the results of ELISA showing the amount of IgM antibody against a canine coronavirus in serum obtained by administration experiment shown in FIG. 4.

Figure 6:
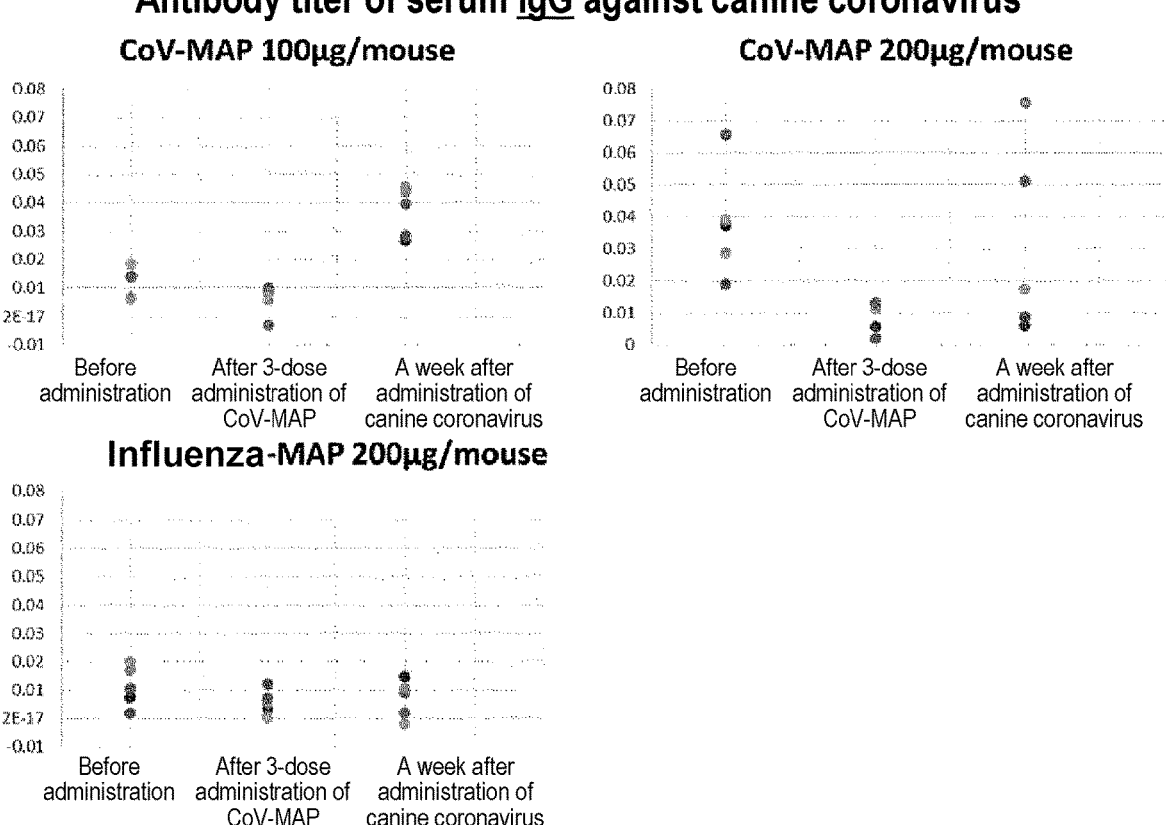

FIG. 6 shows the results of ELISA showing the amount of IgG antibody against a canine coronavirus in serum obtained by the administration experiment shown in FIG. 4.

Figure 7A:
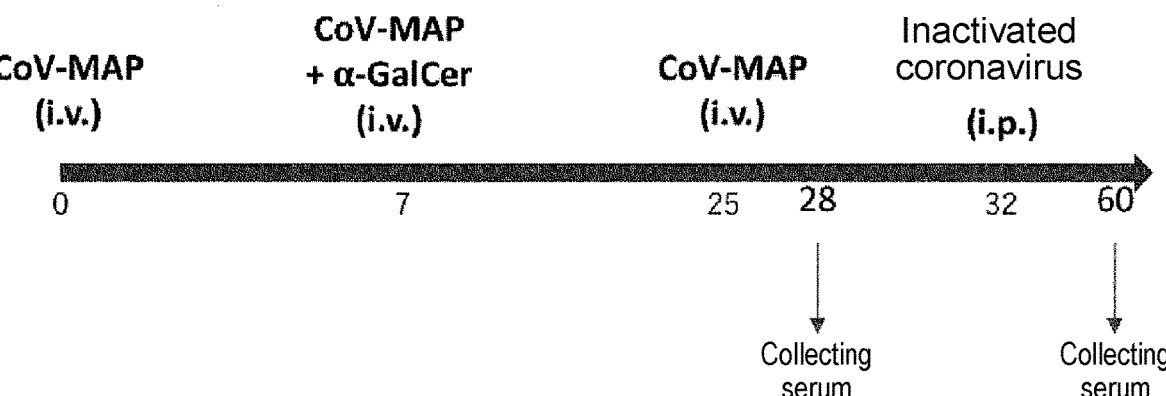

FIG. 7a shows an experimental scheme for administration of the multiple antigen peptide of the present invention (CoV-MAP) followed by an inactivated virus administration simulating infection. CoV-MAP was administered at two doses (200 µg/mouse/vaccination).

Figure 7B:
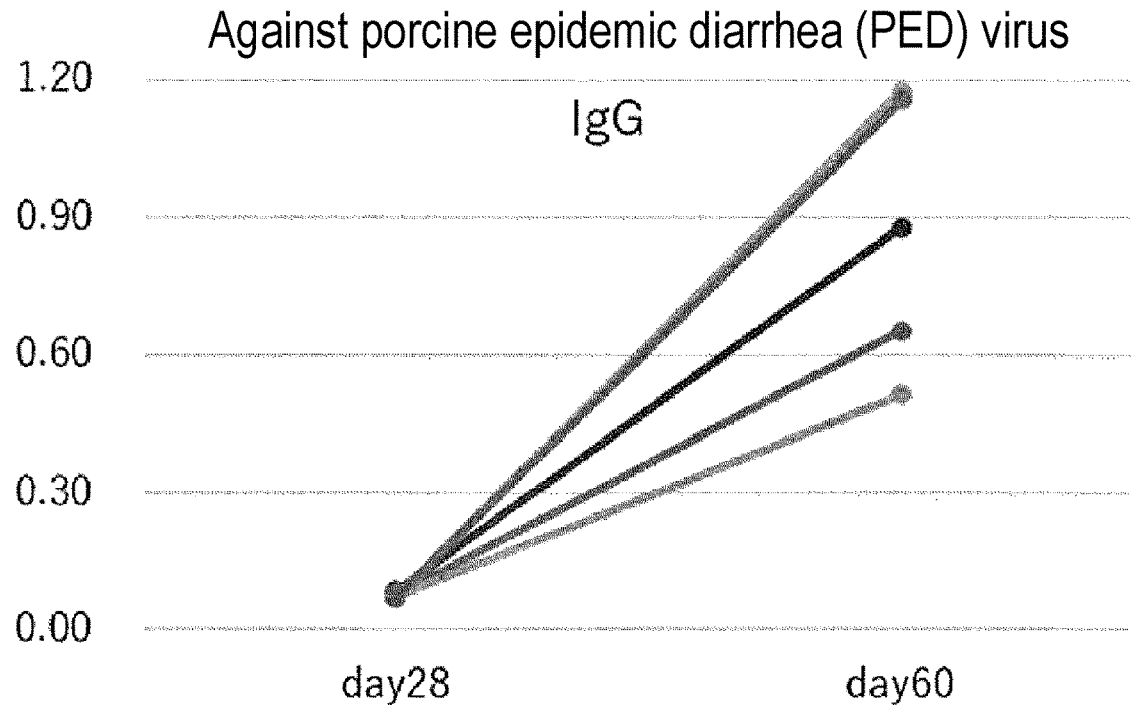

FIG. 7b shows the results of ELISA showing the amount of IgG antibody against a porcine coronavirus (PDE) in serum obtained by the administration experiment shown in FIG. 7a.

Figure 8A:
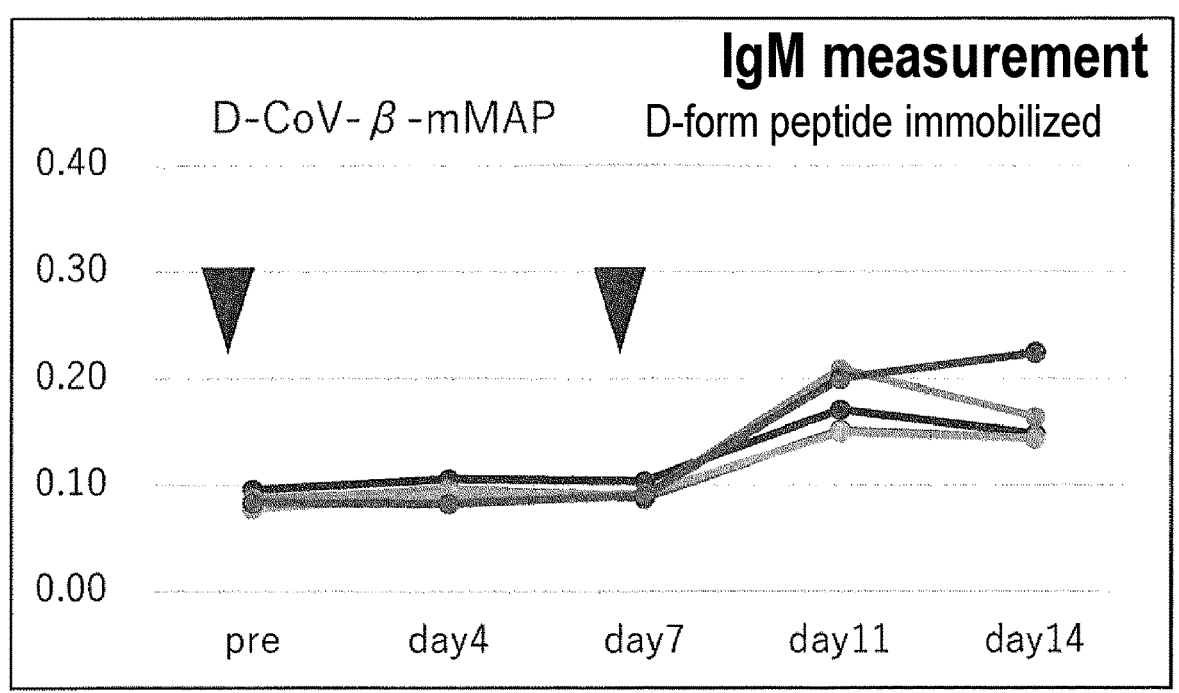

FIG. 8a shows the results of ELISA (D-form peptide immobilization) showing the amount of serum IgM antibody in mice administered with D-CoV-β-MAP which is a CoV-MAP peptide consisting of D-form amino acids.

Figure 8B:
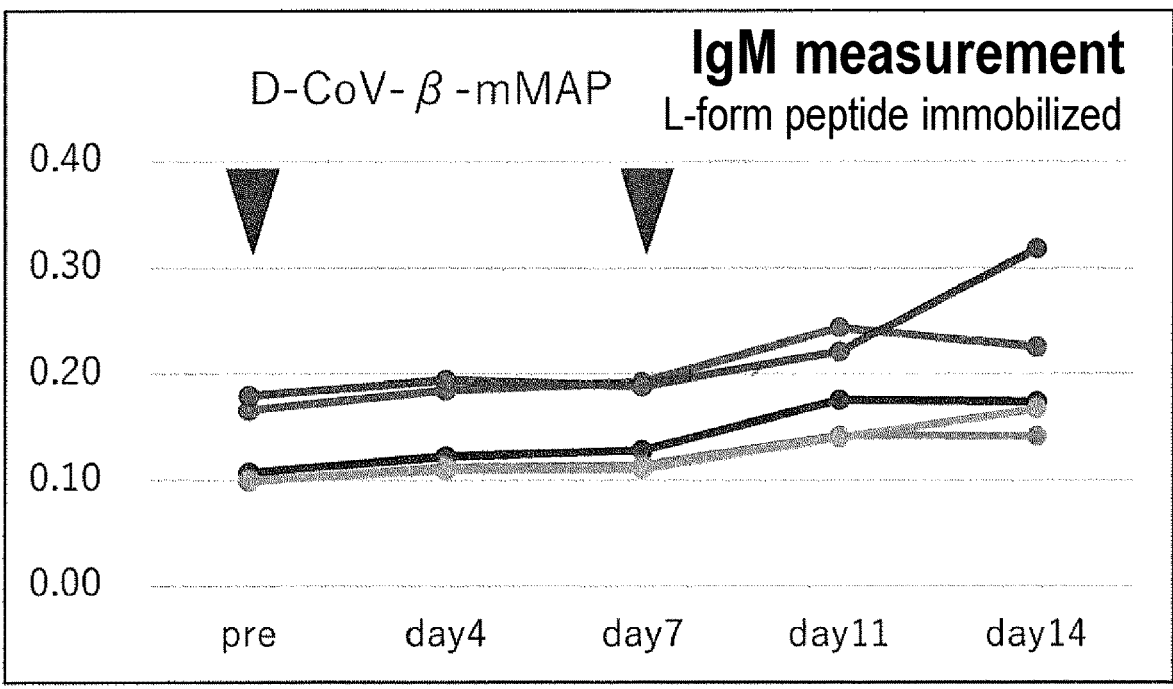

FIG. 8b shows the results of ELISA (L-form peptide immobilization) showing the amount of serum IgM antibody in mice administered with D-CoV-β-MAP which is a CoV-MAP peptide consisting of D-form amino acids.

8

Figure 8C:
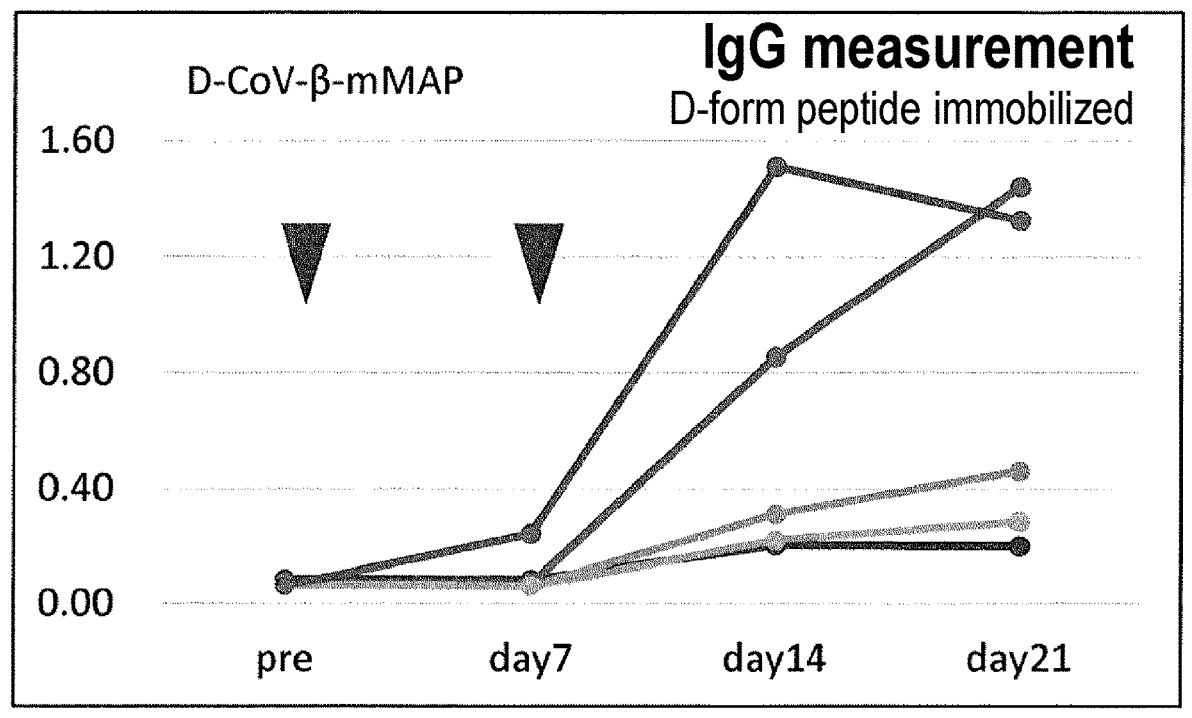

FIG. 8c shows the results of ELISA (D-form peptide immobilization) showing the amount of serum IgG antibody in mice administered with D-CoV-β-MAP which is a CoV-MAP peptide consisting of D-form amino acids.

Figure 8D:
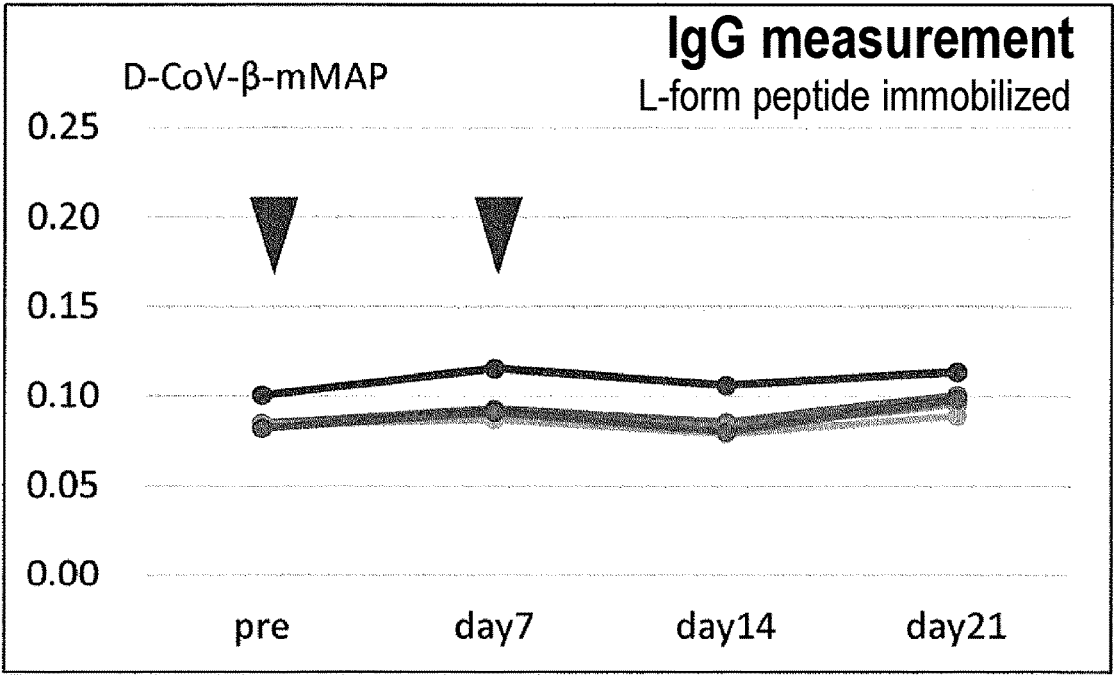

FIG. 8d shows the results of ELISA (L-form peptide immobilization) showing the amount of serum IgG antibody in mice administered with D-CoV-β-MAP which is a CoV-MAP peptide consisting of D-form amino acids.

Figure 9:
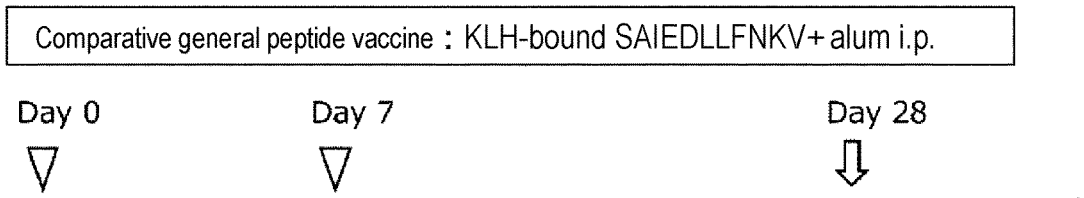

FIG. 9 shows an administration scheme in which an 8 valent CoV-MAP peptide is intravenously administered three times, and thereafter, a boost vaccination with a canine coronavirus was carried out. Cont-MAP represents a first negative control, which is MAP containing a partial peptide of an influenza virus. MAP was intravenously administered at a dose of 200 µg/mouse in three divided potions (Day 0, Day 7 and Day 25). In the second time, CD1d ligand, α-GalCer (in a dose of 0.1 µg/mouse), was intravenously administered in combination with MAP. The boost shot (vaccination) was intraperitoneally made. A second negative control is prepared by mixing a peptide having an amino acid sequence set forth in SEQ ID NO: 8 (short peptide) bound to keyhole limpet hemocyanin (KHL) as an immunogen, with alum, and intraperitoneally administered at a dose of 100 µg/mouse.

Figure 10:
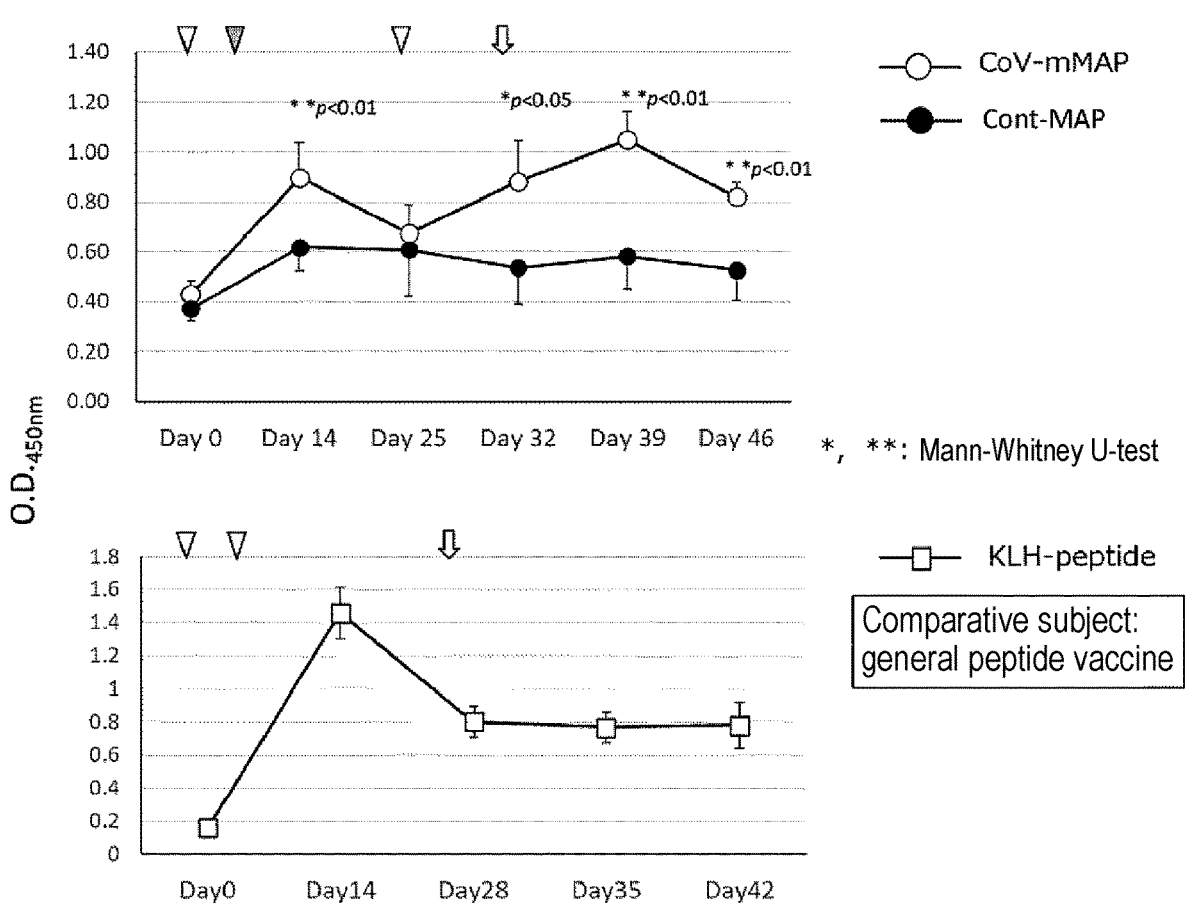

FIG. 10 shows the results of the experiments conducted in accordance with the immunization program (scheme) shown in FIG. 9. FIG. 10 shows IgM production in mouse serum for the short peptide after a serial immunization program. The vertical axis represents IgM production shown by optical density (OD450 value). The horizontal axis represents the number of days elapsed since the first administration.

Figure 11:
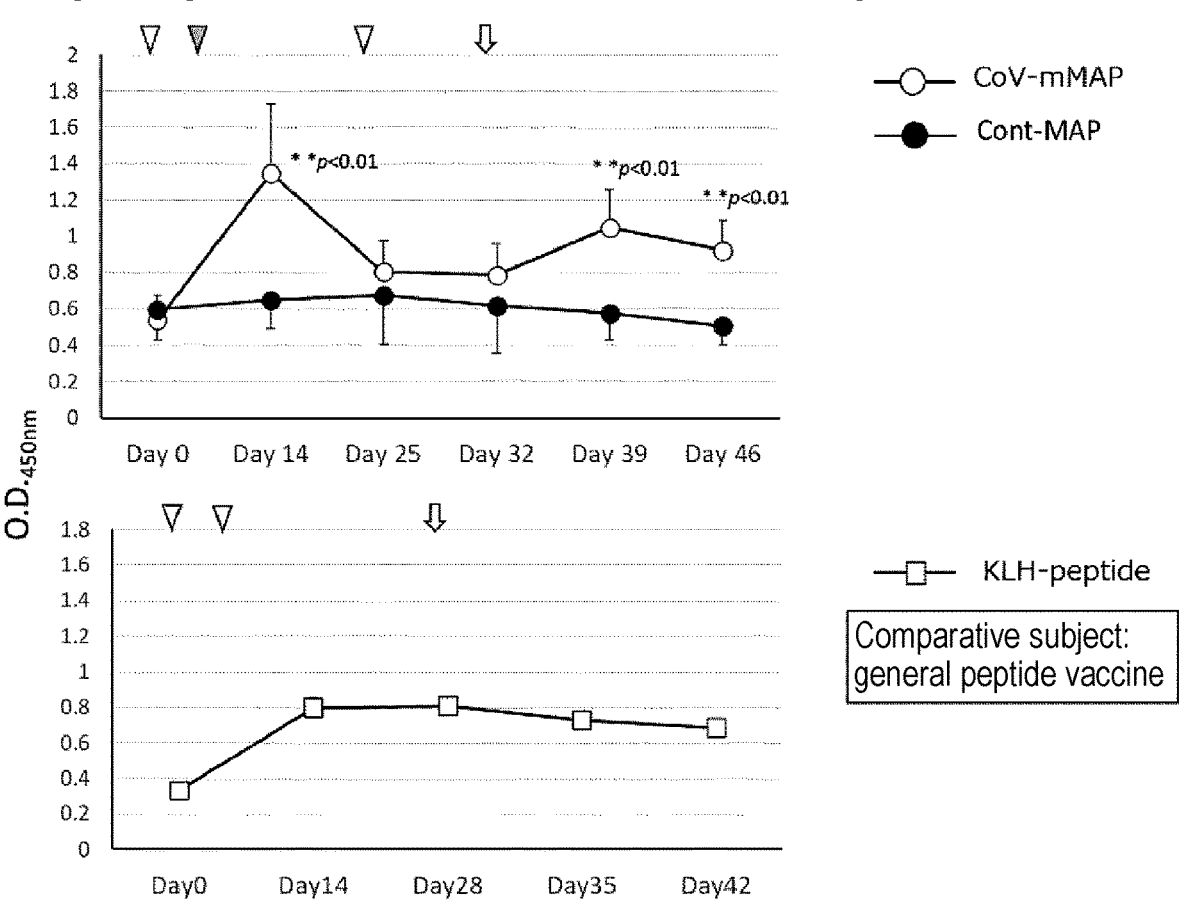

FIG. 11 shows the results of the experiment according to the immunization program of FIG. 9. FIG. 11 shows IgM production against the canine coronavirus antigen in mouse serum after a serial immunization program. The vertical axis represents IgM production shown by optical density (OD450 value). The horizontal axis represents the number of days elapsed since the first administration.

Figure 12:
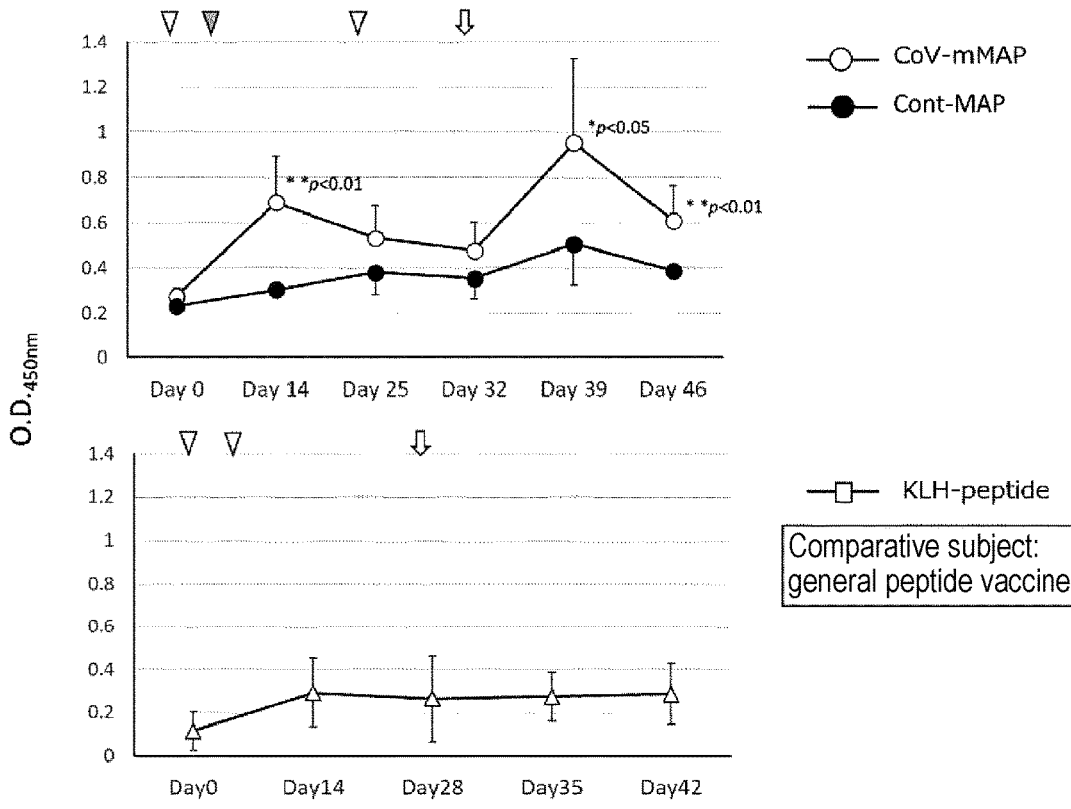

FIG. 12 shows the results of the experiment according to the immunization program of FIG. 9. FIG. 12 shows IgM production against the porcine epidemic diarrhea virus (PDE) antigen in mouse serum after a serial immunization program. The vertical axis represents IgM production shown by optical density (OD450 value). The horizontal axis represents the number of days elapsed since the first administration.

Figure 13:
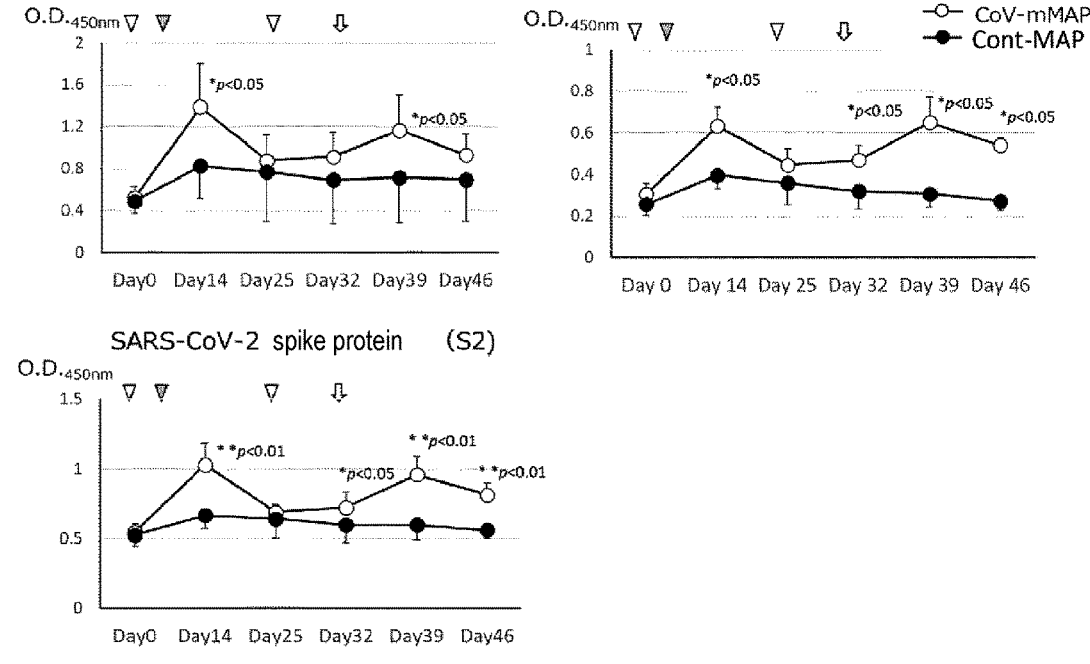

FIG. 13 shows the results of the experiment according to the immunization program of FIG. 9. FIG. 13 shows IgM productions against the SARS-CoV-2 spike protein antigen, the MERS spike protein antigen and the SARS-CoV-2 spike protein (antigen) (S2) in mouse serum, after a serial immunization program. The vertical axis represents IgM production shown by optical density (OD450 value). The horizontal axis represents the number of days elapsed since the first administration.

FIG. 14 show the results of the case where a 4-valent CoV-MAP peptide is administered in accordance with the same scheme as shown in FIG. 9. FIG. 14 shows IgM productions in mouse serum against the short peptide, the porcine epidemic diarrhea virus antigen and the canine coronavirus antigen after a serial immunization program.

FIG. 15 shows productions of various IgM molecules in an animal administered with a MAP having 8-valent No. 2 peptide (having an amino acid sequence set forth in SEQ ID NO: 8 and consisting of all D-form amino acids) in accordance with the same scheme as in FIG. 9.

FIG. 16 shows productions of various IgM molecules in an animal administered with a MAP having 8-valent No. 3 peptide (having an amino acid sequence set forth in SEQ ID NO: 8 in which D-form amino acids are indicated in italics) in accordance with the same scheme as in FIG. 9.

FIG. 17 shows productions of various IgM molecules when MAP having 8 valent No. 4 peptide (having an amino acid sequence set forth in SEQ ID NO: 8 in which D-form amino acids are indicated in italics) was administered in the same scheme as in FIG. 9.

FIG. 18 shows productions of various IgM molecules when MAP having 8 valent No. 5 peptide (having an amino acid sequence set forth in SEQ ID NO: 2 in which D-form amino acids are indicated in italics) was administered in the same scheme as in FIG. 9.

FIG. 19 shows productions of various IgM molecules when MAP having 8 valent No. 6 peptide (having an amino acid sequence set forth in SEQ ID NO: 1) was administered in the same scheme as in FIG. 9.

FIG. 20 shows comparative results of No. 1 peptide to No. 6 peptide.

FIG. 21 shows that IgM production induced by a CoV-MAP peptide (No. 1 peptide) is maintained for a long period of time. In FIG. 21, the amount of serum IgM against each of various antigens on Day 137 after initiation of administration is shown by a ratio relative to the amount of serum IgM before administration.

Figure 22:
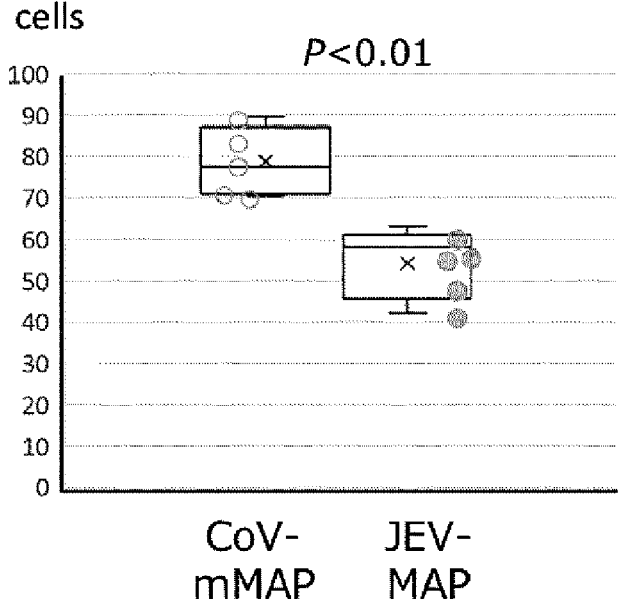

FIG. 22 shows the results of ELISPOT showing that the amount of IgM induced by a CoV-MAP peptide is maintained for a long period of time. The vertical axis represents the number of cells producing an IgM antibody against the peptide in splenocytes. JEV-MAP represents a negative control, which is an 8-valent MAP having a part of Japanese encephalitis virus E protein.

Figure 23:
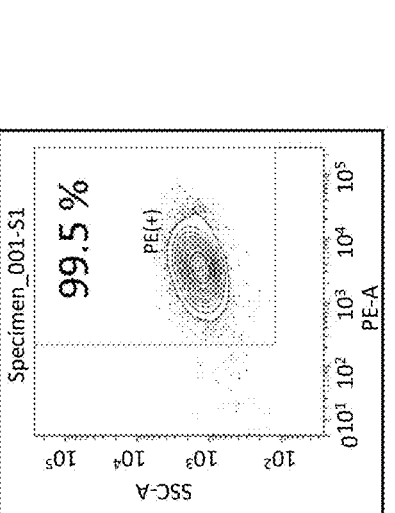

FIG. 23 shows the amount of a CoV-MAP taken up by macrophages. An anti-FLAG tagged monoclonal antibody was used as the positive control. The serum of a non-treatment mouse was used as a negative control.

Figure 24:
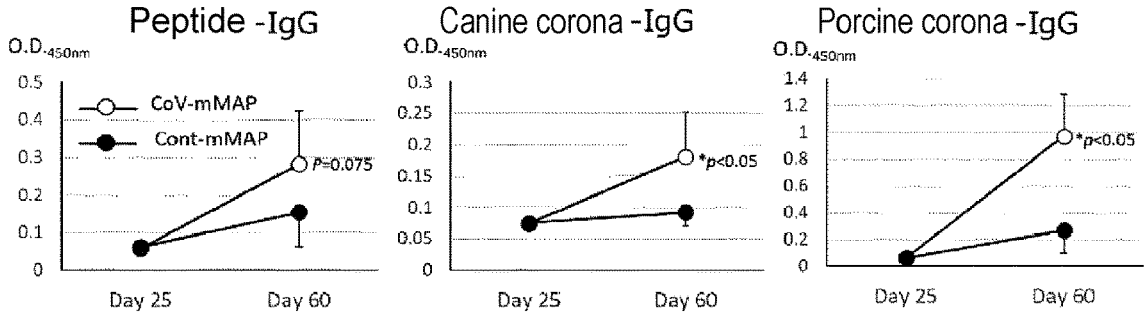

FIG. 24 shows the results of comparing IgG productions in animals administered with a CoV-MAP in accordance with the same scheme as in FIG. 9 before and after boost vaccination.

Figure 25:
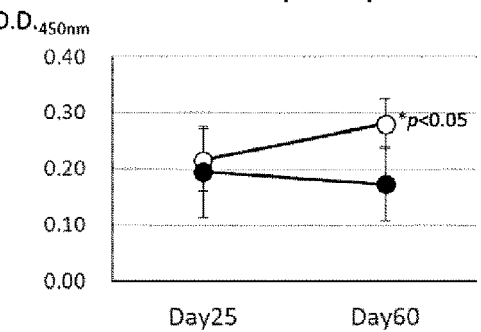

FIG. 25 shows the results of comparing IgG productions in animals administered with a CoV-MAP in accordance with the same scheme as in FIG. 9 before and after boost vaccination.

Figure 26:
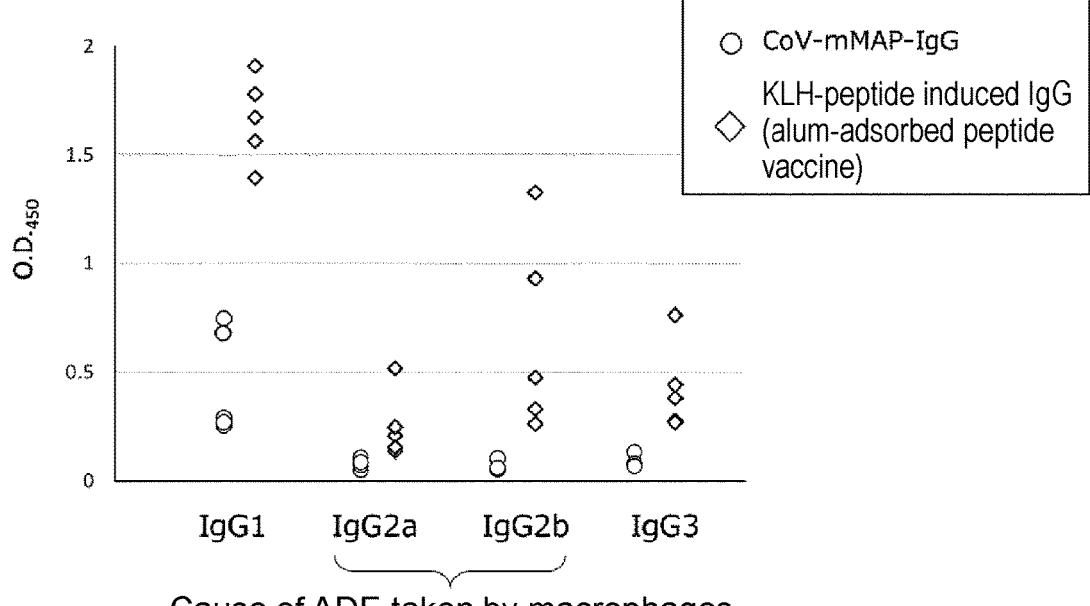

FIG. 26 shows subclasses of IgG produced.

Figure 27:
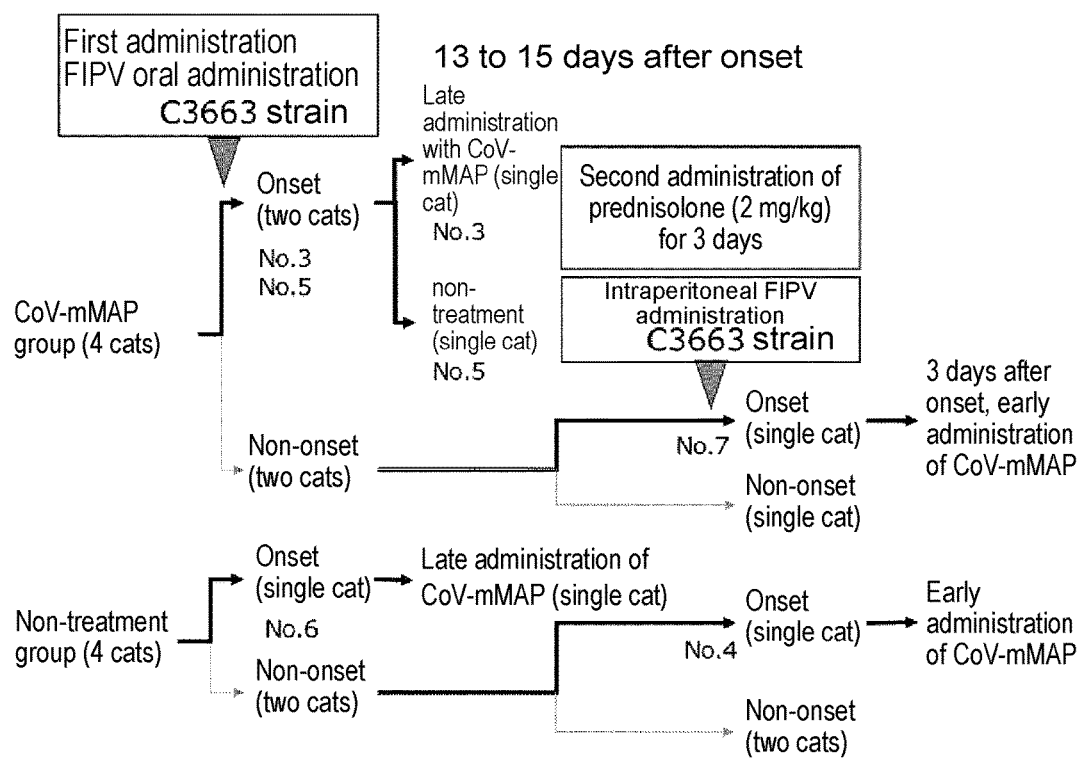

FIG. 27 shows experiments of administering the CoV-MAP before and after infection with feline infectious peritonitis virus (FIPV).

Figure 28:
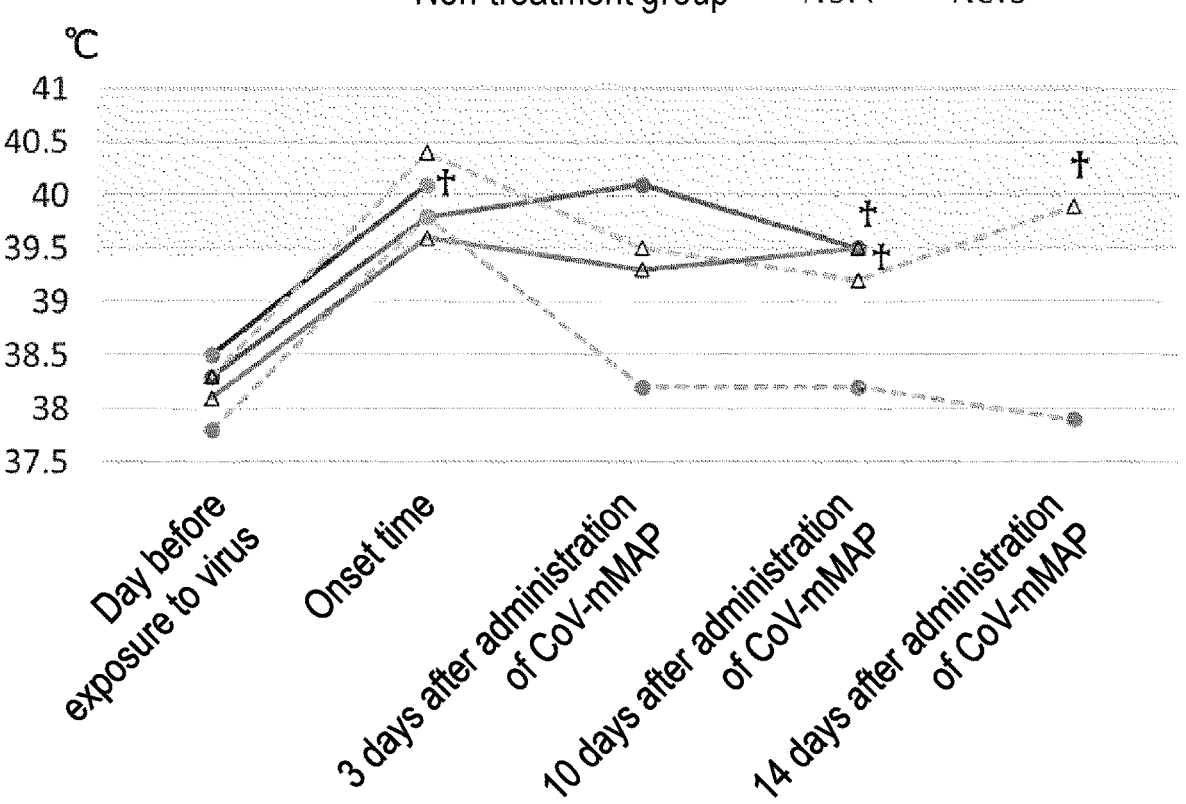

FIG. 28 shows the effect (antipyretic effect) of a vaccine against FIPV infection in the CoV-MAP administration group.

DETAILED DESCRIPTION OF THE INVENTION

In the specification, the "subject" refers to an animal having the immune system, for example, a vertebrate such as a mammal, a fish, a bird, an amphibian and a reptile. Examples thereof include primates such as a human, a chimpanzee, a gorilla, an orangutan, a monkey, a marmoset and a bonobo; quadrupeds (for example, *carnivora, artiodactyl, perissodactyla* and *rodentia*) such as a pig, a rat, a mouse, a cow, a sheep, a goat, a horse, a cat and a dog; and animals belonging to the order of *chiroptera* such as a bat.

In the specification, the "coronavirus" refers to a virus belonging to the family coronavirus of the order Nidovirales. A coronavirus has a plurality of projections consisting of spike proteins (S protein) on the surface envelope structure of a virus particle. Since the electron microscopy image of the projections looks like corona of the sun, the virus is named as a coronavirus. It is known that a coronavirus causes a respiratory infection such as a cold in human. SARS coronavirus (SARS-CoV), MERS coronavirus (MERS-CoV) and 2019 novel coronavirus (SARS-CoV-2) are deadly viruses. Examples of the deadly viruses commonly known include a murine hepatitis virus (MHV) and feline infectious peritonitis virus (FIPV). Vaccines and antiviral drugs for preventing or treating an infection with a coronavirus in humans have not yet been developed at the time of April in 2020. A coronavirus infects a cell when a spike protein exposed on the envelope surface thereof binds to a target cell surface via a cell surface molecule, i.e., angiotensin conversion enzyme 2 (ACE2), and taken into the cell by endocytosis. Examples of the coronavirus include coronaviruses of the coronavirus subfamily such as alpha coronavirus (for example, canine coronavirus, alpha coronavirus 1, huma coronavirus 229E, huma coronavirus NL63, porcine epidemic diarrhea virus); beta coronavirus (for example, subgenus *Embecovirus*, subgenus *Sarbecovirus*, subgenus *Merbecovirus*, subgenus *Nobecovirus*, for example, human intestinal coronavirus 4408, huma coronavirus OC43, mouse coronavirus, huma coronavirus HKU 1, SARS associated coronavirus (for example, SARS coronavirus (SARS-CoV), 2019 novel coronavirus (SARS-CoV-2), MERS coronavirus, equine coronavirus); gamma coronavirus (for example, avia coronavirus, beluga whale coronavirus SW1); and delta coronavirus (for example, bulbul coronavirus HKU11 and Munia coronavirus HKU13, thrush coronavirus HKU12). Examples of the coronavirus include also mutant virus strains of these (particularly, a mutant virus having amino acid sequence of SEQ ID NO: 1 or the amino acid sequence corresponding to SEQ ID NO: 1, such as a mutant virus having an amino acid sequence having addition, insertion, deletion or substitution (for example, conservative substitution: substitution between acidic amino acids, substitution between basic amino acids and substitution between hydrophobic amino acids) of 1 or 2 (preferably 1) amino acids in the amino acid sequence of SEQ ID NO: 1 or 2).

In the specification, the "adjuvant" refers to a substance stimulating the immune response. As the adjuvant, aluminum hydroxide and aluminum phosphate are frequently used.

In the specification, "α-galactosylceramide" refers to glycosphingolipid that can be isolated from a kind of sponge, *Agelas mauritianus*. α-galactosylceramide has the following structure.

[Formula 1]

α-galactosylceramide is a ligand that binds to CD1d and activates NKT cells.

In the specification, "multiple antigen peptide" (MAP) refers to a molecule capable of presenting a plurality of peptides having a predetermined amino acid sequence. The multiple antigen peptide may have a structure consisting of a backbone having a repetitive structure and peptides linked to side chains of the backbone. The backbone and a peptide may be linked via a linker to each other. The multiple antigen peptide may be, for example, a peptide having a dendritic polymer backbone. The multiple antigen peptide having a dendritic polymer backbone has a molecule containing a lysine (Lys) residue as a core and another lysine residue linked to the core via a peptide bond, thereby increasing the number of branches. The number of amino groups and peptides linked thereto for the number "n" of branches is up to $2^n$ {where "n" is a natural number of 2 or more}(Francis, J. P., et al., Immunology, 1991: 73; 249, Schott, M. E., et al., Cell. ImmuNo. 1996: 174: 199-209, Tam, J. P. Proc. Natl. Acad. Sci. 1988: 85; 5409-5413).

In the specification, the "dendritic polymer" (dendrimer) refers to a molecule having a structure regularly branched from a center (core). The dendritic polymer consists of a central molecule called a core and side chains called dendrons. The dendritic polymer has a plurality of arms. Each of the arms of a branch-structure core molecule, further has a plurality of arms, to which molecules forming branches are linked. Such molecules having a plurality of arms and forming a branch are linked to form a dendrimer. In a dendritic polymer, the number of branches repeated from the core in the dendron portion is set forth in "generation". The core molecule is referred to a branch of generation "0" (G0); the primary branch of a dendron provides a first generation (G1) branch and the first-generation branch is further branched to provide a second-generation branch (G2). This is repeated to provide "n" generation branch (Gn).

In the specification, the "lower alkyl group" refers to an alkyl group having, for example, 1 to 4 carbon atoms. The lower alkyl group is, for example, a linear or branched alkyl group. Examples of the linear alkyl group include, a methyl group, an ethyl group, a n-propyl group and a n-butyl group. Examples of the branched alkyl group include an isopropyl group, an isobutyl group, an s-butyl group and a t-butyl group. In the specification, the substituted lower alkyl may be a lower alkyl group having a substituent. The substituent may be selected from the group consisting of a hydroxyl group, a carboxyl group, an amino group, a nitro group, a thiol group, an oxo group and a halogen atom (for example, F, Cl and Br). The number of substituents may be, for example, 1 to 3.

In the specification, the "partial peptide of a coronavirus spike protein consisting of the amino acid sequence corresponding to the amino acid sequence of SEQ ID NO: 1" refers to a partial peptide of a coronavirus spike protein and consisting of the amino acid sequence corresponding to the amino acid sequence set forth in SEQ ID NO: 1 when these sequences are subjected to aligned. Similarly, the "peptide consisting of the amino acid sequence of a coronavirus spike protein and corresponding to an amino acid sequence of SEQ ID NO: 1" is a peptide consisting of the amino acid sequence of a coronavirus spike protein and consisting of the amino acid sequence corresponding to the amino acid sequence of SEQ ID NO: 1. For example, the sequence consisting of amino acid residues 798 to 808 of SEQ ID NO: 1 (GenBank Registration number: AAP30030.1) represents a common amino acid sequence of SARS-CoV-2 and SARS-CoV. The amino acid sequence of SEQ ID NO: 1 has an amino acid sequence (LLF) consisting of 3 amino acids, leucine-leucine-phenylalanine, of the coronavirus spike protein. The LLF sequence is considered as an essential sequence for a coronavirus to infect animal cells. The peptide may contain one or more D-form amino acids.

According to the present invention, there is provided a peptide consisting of the amino acid sequence set forth in SEQ ID NO: 1 or a partial peptide of a coronavirus spike protein consisting of the amino acid sequence corresponding to the amino acid sequence of SEQ ID NO: 1 (or a peptide having the amino acid sequence of a coronavirus spike protein corresponding to the amino acid sequence of SEQ ID NO: 1).

According to the present invention, there is also provided a part of the amino acid sequence set forth in SEQ ID NO: 3, that is, a peptide consisting of an amino acid sequence of 11 to 21 consecutive amino acids in length containing an amino acid sequence set forth in SEQ ID NO: 1 or a partial peptide of a coronavirus spike protein consisting of an amino acid sequence corresponding to the amino acid sequence of 11 to 21 consecutive amino acids in length. The 11 to 21 amino acids in length refers to 11, 12, 13, 14, 15, 16, 17, 18, 19, 20 or 21 amino acids in length. The same applies hereinafter in the specification.

According to the present invention, there can be provided a peptide consisting of an amino acid sequence of 11 to 21 consecutive amino acids in length of a spike protein of feline infectious peritonitis virus (FIPV) and containing an amino acid sequence set forth in SEQ ID NO: 2. According to the present invention, there is further provided a peptide having an amino acid sequence of FIPV spike protein corresponding to the above peptide.

According to the present invention, there is provided a peptide consisting of an amino acid sequence of 11 to 21 consecutive amino acids in length of a spike protein of porcine epidemic diarrhea virus (PEDV) and containing the amino acid sequence set forth in SEQ ID NO: 6. According to the present invention, there is further provided a peptide having an amino acid sequence of PEDV spike protein and corresponding to the above peptide.

According to the present invention, there is provided a peptide consisting of an amino acid sequence of 11 to 21 consecutive amino acids in length of a spike protein of a canine coronavirus and having the amino acid sequence corresponding to the amino acid sequence of SEQ ID NO: 1. According to the present invention, there is further provided a peptide having an amino acid sequence of a spike protein of PEDV and corresponding to the above peptide.

In the specification, these peptides will be sometimes referred to as the peptide of the present invention.

The peptide of the present invention is isolated or purified. The peptide of the present invention may be artificially synthesized.

A peptide consisting of the amino acid sequence of SEQ ID NO: 1 has 11 amino acids in length. A peptide consisting of the amino acid sequence of SEQ ID NO: 1 can induce an antibody specific to a coronavirus by integrating it into a multiple antigen peptide. The amino acid sequence of SEQ ID NO: 1 is conserved in a wide variety (all) of viruses of the family coronavirus. In contrast, a peptide containing the amino acid sequence and its continuous amino acid sequence may have a high tendency toward a predetermined coronavirus.

A partial peptide of a coronavirus spike protein consisting of the amino acid sequence corresponding to the amino acid sequence of SEQ ID NO: 1 is the same as defined above. In an embodiment, in the partial peptide, the amino acid sequence corresponding to SEQ ID NO: 1 may have any one of addition, insertion, substitution and deletion of one base in the amino acid sequence of SEQ ID NO: 1. In an embodiment, the partial peptide may have an amino acid sequence set forth in SEQ ID NO: 7: $SX_1IEDLLFX_2$ KV wherein $X_1$ represents, F, A or V and $X_2$ represents D or N. In a preferable embodiment, the partial peptide may have an amino acid sequence set forth in SEQ ID NO: 2 or 6. Examples of the substitution include conservative substitutions (for example, substitution between acidic amino acids, substitution between basic amino acids and substitution between hydrophobic amino acids). The amino acid sequence set forth in SEQ ID NO: 2 represents a partial peptide of a feline infectious peritonitis virus (FIPV) spike protein and has a sequence corresponding to the amino acid sequence of SEQ ID NO: 1.

According to the present invention, there is provided a multiple antigen peptide (hereinafter sometimes referred to as "the multiple antigen peptide of the present invention") containing the peptide of the present invention. In the multiple antigen peptide, the peptide of the present invention is linked to the tail end of the dendritic polymer backbone. The tail end and the peptide of the present invention may be linked via a linker to each other. The linkage can be made by a covalent bond. The linker is not particularly limited as long as it does not significantly prevent presentation of a peptide. A chemically stable linker such as polyethylene glycol and a flexible linker (for example, non-peptide linker or a peptide linker) can be used. The chemically stable linker can be stable at least under physiological conditions. As the linker, a peptide linker may be used. As the peptide linker, a flexible linker such as a GS linker and a linker having a secondary structure such as an alpha helix structure or a β sheet structure can be used. The multiple antigen peptide of the present invention may contain one or more peptides of the present invention. In a preferable embodiment, the multiple antigen peptide of the present invention may contain 4 or more peptides of the present invention. In a preferable embodiment, the multiple antigen peptide of the present invention may contain 8 or more peptides of the present invention. The multiple antigen peptide of the present invention is preferably isolated or purified.

In an embodiment of the present invention, the multiple antigen peptide of the present invention is a multiple antigen peptide containing a dendritic polymer backbone and the multiple antigen peptide of the present invention, wherein the core of the dendritic polymer is a lysine residue, the lysine residue is regarded as "0"-generation, satisfying the following Requirement 1 where k is any natural number from 1 to n, and the peptide of the present invention is linked to each of the amino groups of lysine of the "n" generation:

Requirement 1: To each of the amino groups of the "k−1" generation lysine residue, the "k" generation lysine residue is linked via a peptide bond.

In the above embodiment, "n" represents 2, 3, 4, 5, 6, 7, 8, 9 or 10, preferably, 2, 3 or 4 and more preferably 2 or 3. More specifically, in the embodiment of the present invention, there is provided a multiple antigen peptide of 4 to $2^{n+1}$ valences.

In an embodiment of the present invention, the multiple antigen peptide of the present invention may be a multiple antigen peptide containing a dendritic polymer backbone and the multiple antigen peptide of the present invention, wherein the core of the dendritic polymer is a lysine residue; to each of the two amino groups of the lysine residue, a lysine residue forming a first-generation branch is linked via a peptide bond; and to each of the amino groups of the lysine resides forming a first-generation branch, the peptide of the present invention is linked, and contain 4 peptides.

In an embodiment of the present invention, the multiple antigen peptide of the present invention may be a multiple antigen peptide containing a dendritic polymer backbone and the multiple antigen peptide of the present invention (the core of the dendritic polymer is a lysine residue; to each of the two amino groups of the lysine residue, a lysine residue forming a first-generation branch are linked via a peptide bond; and to each of the amino groups of the lysine resides forming a first-generation branch, a lysine residue forming a second-generation branch is linked via a peptide bond; to each of the amino groups of the lysine residues forming a second-generation branch, the peptide of the present invention is linked, and contain 4 to 8 peptides mentioned above (more specifically, 4-valent to 8-valent multiple antigen peptide).

In a preferable embodiment, the multiple antigen peptide of the present invention may be a 4-valent multiple antigen peptide (MAP-4) having a structure set forth in the following formula (I) or an 8-valent multiple antigen peptide (MAP-8) having a structure set forth in the following formula (II). Four valent to $2^{n+1}$ valent (MAP-$2^{n+1}$) multiple antigen peptides corresponding to the generation number "n" of branches are provided.

[Formula 2]

(I)

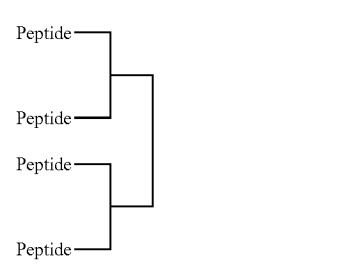

-continued

[Formula 3]

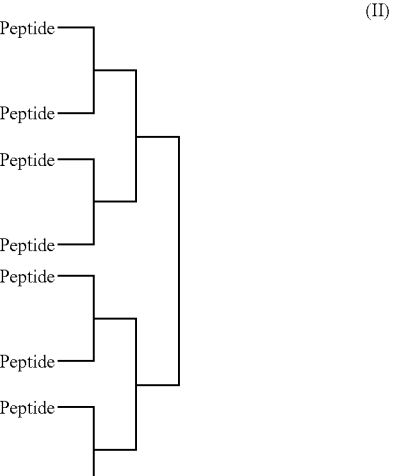

(II)

These multiple antigen peptides can be synthesized by introducing a peptide to a dendritic backbone immobilized on a resin. More specifically, a multiple antigen peptide (MAP-4) having a structure set forth in the following formula (III) can be prepared by introducing a peptide to amino groups of a backbone, for example, a dendric polymer backbone, having a core lysine residue and 2 lysine residues forming a first-generation branch. The core lysine residue may be immobilized on the resin.

[Formula 4]

(III)

wherein lines represent peptide bonds formed by an aminobutyl group and amino group from a lysine residue.

A multiple antigen peptide (MAP-8) having a structure of the following formula (IV), for example, can be prepared by introducing a peptide to amino groups of a backbone having a core lysine residue and 2 lysine residues forming a first-generation branch and 4 lysine residues forming a second-generation branch as a dendritic polymer backbone as mentioned above. The core lysine residue may be immobilized on a resin.

[Formula 5]

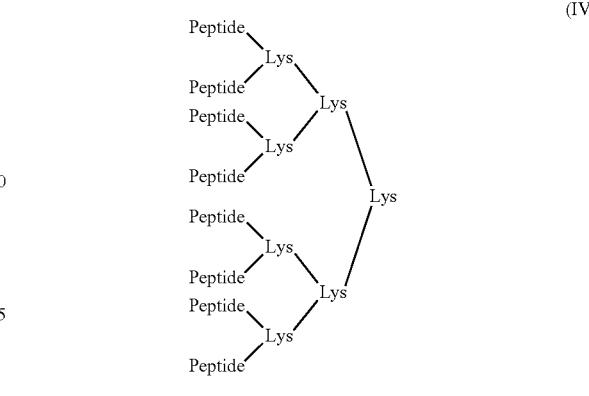

(IV)

wherein lines represent peptide bonds formed by an aminobutyl group and amino group from a lysine residue.

In a preferable embodiment, the multiple antigen peptide of the present invention may have a structure set forth in formula (III) or (IV) wherein the peptide is the peptide of the present invention. More specifically, in an embodiment, the multiple antigen peptide of the present invention may be a peptide formed by linking a peptide to 4 amino groups of lysine residues of a backbone of dendritic polymer (which is formed by linking 2 lysine residues forming a first-generation branch to an aminobutyl group and amino group of a core lysine residue via a peptide bond) via a peptide bond or a chemically stable bond other than a peptide bond. In an embodiment, the multiple antigen peptide of the present invention may be a peptide formed by linking a peptide to 8 amino groups of lysine residues of a backbone of a dendritic polymer (which is formed by linking 2 lysine residues forming a first-generation branch to an aminobutyl group and amino group of a core lysine residue via a peptide bond and linking 4 lysine residues forming a second-generation branch to the respective aminobutyl groups and amino groups of the 2 lysine residues via a peptide bond), via a peptide bond or a chemically stable bond other than a peptide bond. Such a peptide can be formed by immobilizing Lys serving as a core by a method known to those skilled in the art and polymerizing Lys to two amino groups of Lys in accordance with the Fmoc method to prepare a dendritic polymer backbone, and then, further polymerizing a peptide to amino groups of lysine residues of the dendritic polymer backbone obtained. Alternatively, to the amino groups of a lysine residue of the obtained dendritic polymer backbone, an azide group is introduced and a peptide can be linked to the dendritic polymer backbone by click chemistry.

In a preferable embodiment, the multiple antigen peptide of the present invention may have a structure set forth in the following formula (VI).

[Formula 6]

(VI)

wherein R represents -linker-peptide or -peptide. The peptide contains the amino acid sequence of the peptide of the present invention; $R^2$ represents a hydrogen atom, an OH group, a substituted or unsubstituted lower alkyl group, having the structure of formula (VI) to amino groups of the "0"-generation lysine residue in formula (VI) via the carboxyl group of the lysine. Similarly, the structure of each of MAP-$2^{n+1}$ having an "n"-generation branch can be defined.

[Formula 7]

(VIII)

amino group, amino acid (for example, 3-aminopropanoic acid (β-alanine), more specifically, —NH—$C_2H_4$—COOH), a halogen atom or a peptide; the amino acid can be linked to the above molecule via an amide bond. Note that, MAP-8 may have a structure formed by linking two compounds wherein $R^2$ is the same as defined above.

In the above, the linker can be polyethylene glycol (PEG). In a preferable embodiment, PEG can be polyethylene glycol having a degree of polymerization of, for example, 2 to 30, 5 to 20 or 10 to 15.

In the above, the peptide consists of the peptide of the present invention or contains the peptide of the present invention and a linker peptide. The linker peptide may be, for example, a flexible linker or a peptide forming a β sheet structure.

A compound having a structure set forth in the above formula (VI) can be obtained by reacting a peptide or a peptide-linker compound to an acetylene group (—C≡CH) of a compound having a structure set forth in the following formula (VII), by click chemistry, more specifically, by reacting, to a compound having a structure set forth in the following formula (VII), a peptide-azide group (having an azide group at an end) or a peptide-linker-azide group in the presence of a monovalent copper ion. The peptide-azide group and peptide-linker-azide group can be obtained by a commonly known method, for example, converting the N terminal of a peptide (obtained by a commonly known method) to an azide group or performing a condensation reaction of a linker part having an azide group and a carboxyl group respectively at the two ends.

[Formula 8]

(VII)

wherein $R^2$ is the same as defined above.

A compound set forth in formula (VII) is a synthetic intermediate of a compound set forth in formula (VI) and obtained by linking, to amino groups of a lysine residue providing a first-generation branch, an artificial amino acid having an acetylene group at a side chain, for convenience of a reaction, via a peptide bond, to form a reactive acetylene group at an end (see, for example, WO2015190555A). Note that, a synthetic intermediate of MAP-8 may have a structure obtained by linking two compounds having a structure of formula (VII) via a carboxylic group of a "o"-generation lysine in formula (VII), to each of amino groups of the lysine residue. Similarly, the structure of a synthetic intermediate of MAP-$2^{n+1}$ having an "n"-generation branch can be defined.

The multiple antigen peptide of the present invention can be prepared in accordance with a method disclosed, for example, in WO2018/084247A. The lysine backbone of MAP can be prepared by polymerizing lysine whose two amino groups are protected, for example, with a 9-fluorenylmethyloxycarbonyl group (Fmoc group), in accordance with the Fmoc method. The peptide can be further elongated from the amino group of a lysine residue in accordance with the Fmoc method. The Fmoc method can be appropriately carried out by those skilled in the art using commonly known techniques. The Fmoc method can be carried out on a solid support. Examples of the solid support that can be used include Wang resin, HMPA resin, HMBA resin and NovaSyn TGT resin. The method of synthesizing a peptide on a solid support is called solid phase synthesis, which is known to those skilled in the art. As mentioned above, the multiple antigen peptide of the present invention can be appropriately prepared by those skilled in the art in accordance with a routine method.

In a preferable embodiment, the multiple antigen peptide of the present invention may be a multiple alloantigen peptide. In the multiple alloantigen peptides, all antigenic peptides have the same amino acid sequence.

In another preferable embodiment, the multiple antigen peptide of the present invention may contain a peptide having two or more different amino acid sequences as an antigenic peptide.

In the present invention, the multiple antigen peptide of the present invention can be used for inducing immunity (particularly, antigen-specific immunity) by administering it to a subject. In the present invention, the multiple antigen peptide of the present invention can be used for inducing an antigen-specific antibody production by administering it to a subject. In the present invention, the multiple antigen peptide of the present invention can be used for inducing an antibody against a coronavirus by administering it to a subject.

In the present invention, there is provided a vaccine containing the multiple antigen peptide of the present invention (sometimes referred to as "the vaccine of the present invention").

The vaccine of the present invention is effective for a wide variety of coronaviruses. The vaccine of the present invention can be effective for SARS-CoV-2. The vaccine of the present invention can be effective for feline infectious peritonitis virus (FIPV).

The vaccine of the present invention may not be used in combination with an adjuvant (for example, an aluminum salt such as aluminum hydroxide, aluminum phosphate and aluminum potassium sulfate; e.g., incomplete Freund adjuvant, complete Freund adjuvant, liquid paraffin, lanolin, settable adjuvant) stimulating helper T cells (or T cells dependent immunity) and is preferably not used in combination with an adjuvant. The vaccine of the present invention may not contain an adjuvant (for example, an aluminum salt such as aluminum hydroxide, aluminum phosphate, aluminum potassium sulfate; e.g., incomplete Freund adjuvant, complete Freund adjuvant, liquid paraffin, lanolin, settable adjuvant) and preferably does not contain an adjuvant. However, the vaccine of the present invention can be preferably used in combination with an agent not stimulating helper T cells (T cells dependent immunity) such as α-galactosylceramide.

The vaccine of the present invention may contain the multiple antigen peptide of the present invention and a pharmaceutically acceptable carrier and/or an excipient. The vaccine of the present invention may be parenterally administered (for example, intravenous administration, intradermal administration, subcutaneous administration, intramuscular administration, intraperitoneal administration, nasal administration, transmucosal administration, inhalation administration). Accordingly, as the pharmaceutically acceptable carrier and/or an excipient, a carrier and/or an excipient suitable for parenteral administration (for example, intravenous administration, intradermal administration, subcutaneous administration, intramuscular administration, intraperitoneal administration, nasal administration, transmucosal administration, inhalation administration) can be used. Examples of the pharmaceutically acceptable carrier and/or excipient include a salt, a buffer, a pH regulator, isotonic agent, a preservative and water.

According to the present invention, the vaccine may be a composition for use in producing an antibody against a coronavirus or establishing (producing) immunity against a coronavirus in a subject.

According to the present invention, there is provided the multiple antigen peptide of the present invention for use in producing an antibody against a coronavirus in a subject. According to the present invention, there is provided the multiple antigen peptide of the present invention for use in producing an antibody against a coronavirus in a subject.

According to the present invention, there is provided use of the peptide of the present invention in production of a vaccine. According to the present invention, there is provided use of the multiple antigen peptide of the present invention in the manufacture of a vaccine. The vaccine may be used in producing an antibody against a coronavirus or establishing (producing) immunity against a coronavirus in a subject.

According to the present invention, there is provided a method for administering an antigenic peptide to a subject, comprising administering the multiple antigen peptide of the present invention to the subject. According to the present invention, there is provided a method for stimulating an antigen-specific immunity in a subject, comprising administering an effective amount of the multiple antigen peptide of the present invention to the subject. According to the present invention, there is provided a method for stimulating an immunity against a coronavirus in a subject, comprising administering an effective amount of the multiple antigen peptide of the present invention to the subject. According to the present invention, there is provided the multiple antigen peptide of the present invention for use in these methods or a pharmaceutical composition containing the multiple antigen peptide of the present invention for use in these methods. According to the present invention, there is provided use of the multiple antigen peptide of the present invention in the manufacture of a medicament for use in these methods.

According to the present invention, there is provided a method for administering an antigenic peptide to a subject, comprising administering the multiple antigen peptide of the present invention to the subject in accordance with a dosing regimen. According to the present invention, the subject may be a subject not infected or infected with a coronavirus (the subject may be asymptomatic) or a subject that developed an infection disease with a coronavirus. The method or multiple antigen peptide of the present invention may prevent infection with a coronavirus, delay onset of an infectious disease with a coronavirus, inhibit onset thereof or cure the infectious state in a subject not infected with a coronavirus, and mitigate the symptom and delay progression of the symptoms (for example, inhibits aggravation), stop progression or relieve the symptoms in a subject that developed an infectious disease. The method or multiple antigen peptide of the present invention can delay onset of a symptom, inhibit onset thereof or cure an infection condition in a subject infected with a coronavirus (for example, a subject before onset), whereas, mitigate a symptom thereof and delay progression of a symptom (for example, inhibits aggravation), stop progression or relieve a symptom in a subject that developed an infectious disease. The method or multiple antigen peptide of the present invention can delay progression (for example, inhibits aggravation) of a symptom, stop progression or relieve a symptom in a subject with an infection disease with a coronavirus. Since the multiple antigen peptide of the present invention mainly induces IgM, the period from administration to antibody induction is short. Thus, the multiple antigen peptide of the present invention can be effective even if administered to a subject infected with a coronavirus and a subject with an infection disease.

According to the present invention, there is provided a method for preventing onset of a symptom in a subject infected with a coronavirus, comprising administering an effective amount of the multiple antigen peptide of the present invention to the subject. The subject infected with a coronavirus in an embodiment may be a subject before onset of an infection disease. The subject infected with a coronavirus may be a subject determined to be infected with a coronavirus by a test (for example, PCR test or antibody test). The subject infected with a coronavirus may be subject determined to be infected with a coronavirus by a test (for example, PCR test or antibody test) and before onset of an infection disease. Owing to the invention, it is possible to delay onset of a symptom, inhibit development of a disease, or cure infection (condition) in a subject.

According to the present invention, there is provided a method comprising administering an effective amount of the multiple antigen peptide of the present invention to a subject before onset of an infection disease with a coronavirus and further comprising administering an effective amount of the multiple antigen peptide of the present invention to the subject after onset. According to the present invention, there is provided a method for administering a peptide to a subject comprising administering the multiple antigen peptide of the present invention to the subject in accordance with a dosing regimen, wherein the dosing regimen comprises administering the multiple antigen peptide of the present invention (for example, 1 to 3 times) to the subject before infection or at a stage considered to be before infection. According to the present invention, there is provided a method for administering a peptide to a subject comprising administering the multiple antigen peptide of the present invention to the subject in accordance with a dosing regimen, wherein the dosing regimen comprises administering the multiple antigen peptide of the present invention 1 to 3 times to the subject before infection or at a stage considered to be before infection and administering the multiple antigen peptide of the present invention once or more after infection or at the stage considered to be after infection. According to the present invention, there is provided a method for administering a peptide to a subject, comprising administering the multiple antigen peptide of the present invention to the subject in accordance with a dosing regimen, wherein the dosing regimen comprises administering the multiple antigen peptide of the present invention 3 times to the subject before infection or at a stage considered to be before infection and administering the multiple antigen peptide of the present invention once or more after infection or at the stage considered to be after infection. In the present invention, owing to booster shot after onset, progression of a symptom of the subject can be delayed (for example, aggravation is inhibited), progression of the symptom can be stopped or the symptom can be relieved. The multiple antigen peptide can be administered at a dose, for example, 1 mg/kg to 3 mg/kg, for example, 1.5 mg/kg per administration. In a preferable embodiment, administration can be made on different days. In a preferable embodiment, administration can be made every day, every other day, every 2 days, every 3 days, every 4 days, every 5 days, every 6 days, every week, every 8-13 days, every 2 weeks, every 15-20 days, in administration intervals of 3 weeks or more. In this embodiment, the subject is, for example, a human, a cat, a dog or a pig. In this embodiment, an infection disease with a coronavirus in a subject can be prevented and/or treated.

In particular, as shown in Examples later described, when the multiple antigen peptide of the present invention, CoV-mMAP, was administered to a cat before infection in accordance with the above dosing regimen, recovery from symptoms of an infection disease (lethality after onset is 100%) with feline infectious peritonitis virus (FIP) was observed. This is considered as a noteworthy effect. According to the present invention, there is provided a pharmaceutical composition containing the multiple antigen peptide of the present invention to be administered in accordance with the above dosing regimen. The pharmaceutical composition can be used for prevention and/or treatment for an infection disease with a coronavirus. According to the present invention, there is provided use of the multiple antigen peptide of the present invention in the manufacture of a medicament to be administered in accordance with the dosing regimen. The medicament can be used for prevention and/or treatment for an infection disease with a coronavirus.

According to the present invention, there is provided a method for preventing and/or treating an infection disease with a coronavirus in a subject in need thereof, comprising administering the multiple antigen peptide of the present invention to the subject. According to the present invention, there is provided a pharmaceutical composition containing the multiple antigen peptide of the present invention for use in the method for preventing and/or treating an infection disease with a coronavirus in a subject in need thereof. According to the present invention, there is provided use of the multiple antigen peptide of the present invention for the manufacture of a medicament to be used in a method for preventing and/or treating an infection disease with a coronavirus in a subject in need thereof.

According to the present invention, there is provided a method for treating an infection disease with a coronavirus in a subject affected with the infection disease, comprising administering an effective amount of the multiple antigen peptide of the present invention to the subject. The subject affected with an infection disease with a coronavirus can be a subject having fever in an embodiment. Since the multiple antigen peptide of the present invention mainly induces IgM, an antibody is induced for a short period of time from administration. Thus, the multiple antigen peptide of the present invention can be effective even if administered to a subject in an early phase of infection. Accordingly, the subject may have any one of symptoms such as olfactory abnormality, dysgeusia, and fever, as early symptoms.

According to the present invention, there is provided a method for preventing aggravation of an infection disease with a coronavirus in a subject affected with the disease, comprising administering an effective amount of the multiple antigen peptide of the present invention to the subject. The subject affected with an infection disease with a coronavirus can be a subject having fever in an embodiment. Since the multiple antigen peptide of the present invention mainly induces IgM, an antibody is induced for a short period of time from administration. Thus, the multiple antigen peptide of the present invention can be effective even if administered to a subject infected (subject in an early phase of infection).

According to the present invention, the coronavirus can be a highly pathogenic coronavirus. The coronavirus is, for example, a coronavirus selected from the group consisting of MERS coronavirus, SARS coronavirus (for example, SARS-CoV, SARS-CoV-2), feline infectious peritonitis virus (FIPV) and porcine epidemic diarrhea virus (PDE).

According to the present invention, the subject can be a human or a non-human mammal. According to the present invention, the pharmaceutical composition and medicament of the present invention can be administered to a human or a non-human mammal.

EXAMPLES

Example 1: Synthesis of Antigenic Peptide

As an antigenic peptide for preparing a vaccine against a coronavirus, a partial peptide of a spike protein which is a surface protein of any one of SARS-CoV, SARS-CoV-2 and feline infectious peritonitis virus (FIPV), was used.

More specifically, the three virus spike proteins were subjected to multiple alignment and a peptide (SEQ ID NO: 1) having an amino acid sequence having 11 consecutive amino acids was prepared (see, FIG. 3).

TABLE 1

| Amino acid sequence information of antigen peptide portion | | |
|---|---|---|
| Type of virus | Amino acid sequence | SEQ ID NO |
| SARS-CoV-2 | $^{816}$SFIEDLLFNKV$^{826}$ | SEQ ID NO: 1 |
| FIPV | $^{963}$SAIEDLLFDKV$^{972}$ | SEQ ID NO: 2 |
| SARS-CoV | $^{798}$SFIEDLLFNKV$^{808}$ | —(The same as SEQ ID NO: 1) |
| PEDV | $^{893}$SVIEDLLFNKV9$^{03}$ | SEQ ID NO: 6 |

* The numbers attached to amino acid sequences represent the amino acid numbers at the terminals of spike proteins.

As shown in Table 1, the partial amino acid sequences consisting of 11 amino acids of SARS-CoV, SARS-CoV-2, feline infectious peritonitis virus (FIPV) and porcine epidemic diarrhea virus (PEDV) were highly homologous.

A peptide having the amino acid sequence of SEQ ID NO: 1 was artificially synthesized based on a routine method to prepare a 4-valent multiple antigen peptide (MAP-4) having a structure set forth in the following formula (I) and an 8-valent multiple antigen peptide (MAP-8) having a structure set forth in the following formula (II).

MAP-8 was prepared by introducing a peptide into a resin having a structure set forth in the following formula (IV).

[Formula 9]

(I)

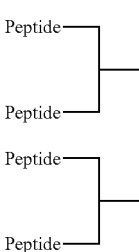

[Formula 10]

(II)

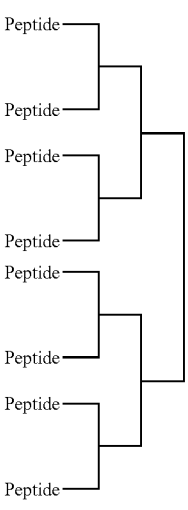

These multiple antigen peptides were synthesized by introducing a peptide into a dendritic backbone immobilized on a resin for efficient synthesis (on the resin). More specifically, MAP-4 was prepared by introducing a peptide into a resin having a dendritic backbone having the structure of the following formula (III).

[Formula 11]

(III)

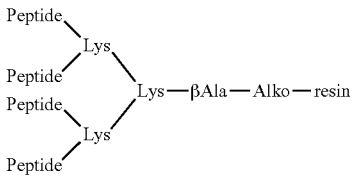

[Formula 12]

(IV)

In the above formula, lysine (Lys) is an amino acid having two amino groups. To each of the amino groups, the carboxyl groups of 2 lysine residues are linked via a peptide bond. As a result, the 2 lysine residues have, in total, 4 amino groups to form a dendritic backbone. To each of the amino groups of the lysine residue, a peptide is introduced via a linker. In this manner, a 4-valent multiple antigen peptide (MAP-4) can be prepared.

MAP-8 was prepared by further dividing each of the terminal lysine (Lys) residues into two and introducing a peptide to a resin having 8 Lys residues having an Fmoc protecting group. To the 4 amino groups of lysine residues of a dendric backbone (having 4 amino groups), carboxyl groups of 4 lysine residues are linked via a peptide bond. As a result, the terminal 4 lysine groups have, in total, 8 amino groups to form a dendric backbone. To each of the amino groups of these lysine residues, a peptide is introduced via a linker to prepare a 4-valent or 8-valent multiple antigen peptide.

A peptide was synthesized by the Fmoc method in accordance with a routine method. More specifically, a peptide was synthesized by swelling a resin, removing an amino acid protecting group at the N-terminal with a deprotection agent, and then, combining another amino acid by a condensation reaction using a coupling reagent and an amino acid derivative. As the coupling reagent, 1-[bis(dimethylamino)methylene]-1H-benzotriazolium 3-oxide hexafluorophosphate (HBTU) and N,N-diisopropylethylamine (DIEA) were used. The peptide was cut from the resin by a TFA cocktail reagent and allowed to precipitate with cold t-butyl methyl ether, washed, collected and dried. After ether was removed. the peptide was dissolved in a 50% aqueous acetonitrile solution, and then, lyophilized.

In introducing a peptide, a linker was introduced into the C terminal of the peptide. In this Example, polyethylene glycol (PEG) was used as the linker. The polyethylene glycol was PEG having a degree of polymerization of 12 (referred to as "PEG (12)").

The structure of MAP-4 was more specifically shown below.

[Formula 13]

(VI)

wherein R represents -PEG (12)-peptide and $R^2$ is the same as defined above

MAP-4 and MAP-8 can be prepared with reference to, for example, WO2018062217A.

The peptide obtained was removed from a resin by use of a 0.1% 2,2,2-trifluoroacetic acid and acetone. The MAP-4 and MAP-8 separated were purified by high performance liquid chromatography to obtain MAP-4 and MAP-8.

Example 2: Administration Experiment

A multiple antigen peptide (MAP-4 and MAP-8, which will be collectively referred to as "CoV-MAP") prepared by linking peptides having the amino acid sequence of SEQ ID NO: 1 in Example 1, was administered to mice in accordance with the scheme shown in FIG. 4. More specifically, CoV-MAP was administered to Balb/c mice at a dose of 100 µg/mouse/vaccination or 200 µg/mouse/vaccination on Day 0, Day 7 and Day 25 through the tail vein. On Day 7, α-galactosylceramide (α-GalCer) was administered at a dose of 0.1 µg through the tail vein. Thereafter, on Day 32, an inactivated canine coronavirus was intraperitoneally administered. As the inactivated canine coronavirus, Vanguard (Ministry of Agriculture, Forestry and Fisheries, protocol 25 animal drug No. 2225, Zoetis-Japan; the same applies hereinafter) was used.

The serum was collected individually on Day 0 (before administration), Day 26 to 31 (after administering CoV-MAP three times) and Day 39 (a week after administration of an inactivated canine coronavirus).

The antibody titers of the serum samples were measured. More specifically, an inactivated canine coronavirus was fixed in the wells of a 96-well plate. As a background control, ovalbumin-conjugated alum was used in place of the inactivated canine coronavirus, and fixed in a well, and the titer thereof was measured.

As a measurement system, an ELISA method using peroxidase as a chromogenic reporter was used. The O.D. values of two wells under the same condition were averaged. The O.D. value of the background well was subtracted from that of the canine inactivated coronavirus well to obtain a numerical value. To confirm specificity of the reaction, reactivity to a coronavirus peptide was measured by using the serum of mice administered with an influenza-virus MAP in place of CoV-MAP (influenza-MAP 200 µg; MAP having the amino acid sequence set forth in SEQ ID NO: 5 was separately prepared in accordance with WO2018084247A).

The results of the CoV-MAP administration experiment were shown in FIGS. 5 and 6. FIG. 5 shows a change of serum IgM antibody titer and FIG. 6 shows a change of serum IgG antibody titer.

As shown in FIG. 5, the antibody titer of serum IgM increased in the serum after administration of CoV-MAP three times and increased or the same after administration of the inactivated canine coronavirus. In contrast, in mice administered with an influenza-virus MAP, the antibody titer against a canine coronavirus did not increase.

As shown in FIG. 6, the antibody titer of serum IgG increased a week after administration with a canine coronavirus. In contrast, in mice administered with the influenza-virus MAP, the antibody titer against a canine coronavirus did not increase.

Example 3: Administration Experiment with Canine Coronavirus Vaccine

CoV-MAP (200 µg/mouse/vaccination) prepared in accordance with Example 1 was administered to mice Day 0, Day 7 and Day 25 as described in the scheme shown in FIG. 7a. On Day 7, α-galactosylceramide (0.1 µg) was administered through the tail vein. As the control, 2E5-MAP was administered in place of CoV-MAP. 2E5-MAP is a MAP containing a partial peptide of influenza-virus hemagglutinin, more specifically, a partial peptide designed for a common amino acid sequence between H3 belonging to group 1 and Hi belonging to group 2. More specifically, 2E5-MAP was a MAP containing 8 sequences each having DGWYG-FRHQNSEGTGQAADLKSTQA (SEQ ID NO: 5). Thereafter, on Day 32, viral infection was simulated by intraperitoneally administering 50 μL of Vanguard, as an inactivated canine coronavirus vaccine.

The serum was collected on Day 28 (before viral infection) and Day 60 (after viral infection) and the antibody titer in the serum samples was checked by ELISA. In ELISA, a system where a porcine epidemic diarrhea virus (PED) antigen was immobilized, was used.

The results were shown in FIG. 7b. Shown in FIG. 7b, it was confirmed that IgG is significantly induced after administration of Vanguard in the system where a PED antigen was immobilized. As the PED antigen, a porcine epidemic diarrhea vaccine, Nisseiken PED live vaccine, was inactivated by heating at 60° C. for 10 hours and put in use.

MAP-8 having the same configuration as above was prepared except that all amino acids of the amino acid sequence of SEQ ID NO: 1 were replaced with D-form amino acids; and a peptide (SEQ ID NO: 4), which was prepared by linking a peptide forming a 3 sheet structure to the front and back thereof, was used as a peptide linker and linked to the C terminal of the resultant amino acid sequence. The resultant CoV-mMAP was administered at a dose of 200 μg/mouse/vaccination through the tail vein (triangles in FIGS. 8a and 8b). In the second administration, α-galactosylceramide (0.1 μg/mouse) was used in combination. ELISA was carried out by use of a plate on which a D-form peptide, which was obtained by replacing all amino acids of a peptide consisting of the amino acid sequence of SEQ ID NO: 1 with D-form amino acids, was immobilized.

The results were shown in FIGS. 8a to 8d. As shown in FIGS. 8a to 8d, D-form CoV-mMAP also induced both IgM and IgG. Therefore, it was demonstrated that the amino acid sequence may consist of D-form amino acids. It was also found that if an antigenic peptide and the backbone of a multiple antigen peptide are linked via a peptide linker (for example, linker capable of forming a β sheet structure), antibody induction was not inhibited.

CoV-mMAP was administered in accordance with the dosing scheme (regimen) shown in FIG. 9, and thereafter, boost vaccination was carried out with a canine coronavirus vaccine antigen. As a negative control (Cont-MAP), 8-valent MAP having a partial peptide of an influenza virus was used. As a general peptide vaccine, an antigen was prepared by linking an amino acid sequence set forth in SEQ ID NO: 8 to not a MAP but a keyhole limpet hemocyanin and mixed with alum, and then, intraperitoneally administered. A serum sample was taken Day 0, Day 14, Day 25 day, Day 32, Day 39 and Day 46, and then, IgM levels in the serum samples were measured. The vaccine effect was evaluated based on the amounts of peptide specific IgM and viral antigen-specific IgM in the serum samples.

First, vaccine effect was evaluated based on the level of serum IgM bound to a peptide used as an antigen, as an index. Mouse serum (1/200 dilution) was reacted with a BSA fusion antigen peptide immobilized on an ELISA plate at 4° C., overnight. Detection was made in accordance with a routine method including binding a biotin-labeled anti-mouse IgM polyclonal antibody (Southern Biotech) serving as an antibody for detection and further reacting a peroxidase-labeled streptavidin with the antibody for detection. The results were shown in FIG. 10. As shown in FIG. 10, the serum IgM level significantly increased in the CoV-mMAP administration group by two-step immunization. Also, the serum IgM level significantly increased in the CoV-mMAP administration group by boost vaccination. In contrast, in the negative control, the serum IgM level did not significantly increased. In a group of mice administered with the general peptide vaccine commonly used, the serum IgM level temporarily increased after a second immunization but did not increase by boost vaccination. The results suggest that it is difficult to establish (create) immunological memory for IgM production by the general peptide vaccine commonly used.

A vaccine effect was then evaluated based on the level of serum IgM that binds to a canine coronavirus vaccine antigen (liquid vaccine of inactivated canine coronavirus NL-18 strain obtained by feline renal cell line culture, product name, Vanguard Plus CV, company: Zoetis-Japan) as an index. The serum IgM level was measured in the same manner as above by immobilizing the antigen (10 μg/mL) on an ELISA plate and bringing serum into contact with the plate. The results were shown in FIG. 11. As shown in FIG. 11, the serum IgM level significantly increased in the CoV-mMAP administration group through two-step immunization. Also, serum IgM level significantly increased in the CoV-mMAP administration group by boost vaccination. In contrast, in the negative control, serum IgM level did not significantly increase. In a group of mice administered with the general peptide vaccine commonly used, the serum IgM level increased after a second immunization but did not increase by boost vaccination. The results suggest that it is difficult to establish (create) immunological memory for IgM production by the general peptide vaccine commonly used.

Further, vaccine effect was evaluated based on the level of serum IgM bound to a porcine epidemic diarrhea virus (PED) vaccine (inactivated porcine epidemic diarrhea virus P-5V, Nisseiken Co., Ltd.) as an index. The serum IgM level was measured in the same manner as above by inactivating a live vaccine by incubating it at 60° C. for 10 hours, immobilizing the vaccine on an ELISA plate and bringing the serum into contact with the plate. The results were shown in FIG. 12. As shown in FIG. 12, the serum IgM level significantly increased in the CoV-mMAP administration group through two-step immunization. Also, the serum IgM level significantly increased in the CoV-mMAP administration group by boost vaccination. In contrast, in the negative control, the serum IgM level did not significantly increase. In a group of mice administered with the general peptide vaccine commonly used, the serum IgM level slightly increased after a second immunization but did not increase at all by boost vaccination. The results suggest that it is difficult to establish (create) immunological memory for IgM production by the general peptide vaccine commonly used and that IgM that commonly reacts with the peptide, canine coronavirus antigen and PED virus antigen, cannot be induced.

Further, vaccine effect was evaluated based on the levels of serum IgM against each of SARS-CoV-2 spike protein (full length), MERS spike protein and SARS-CoV-2 spike protein (S2 subunit) as indexes. MERS recombinant spike protein (Sino Biological) and SARS-CoV-2 recombinant spike protein (Invitrogen) and a recombinant S2 subunit protein thereof (Ray Biotech) were each (5 μg/ml) immobilized and allowed to be in contact with serum in the same manner as above to measure the serum IgM level in the same manner as above. The results were shown in FIG. 13. As shown in FIG. 13, the serum IgM level significantly increased in the CoV-mMAP administration group through two-step immunization. Also, the serum IgM level significantly increased in the CoV-mMAP administration group by boost vaccination. In contrast, in the negative control, the serum IgM level did not significantly increase. From the results, it was found that CoV-mMAP also induces IgM reactive to a highly pathogenic coronavirus in humans.

Four-valent CoV-mMAP was prepared in the same manner as in 8-valent CoV-mMAP. Four-valent CoV-mMAP was administered in accordance with the dosing scheme (regimen) shown in FIG. 9, and thereafter, a boost vaccination was carried out by intraperitoneally administering a canine coronavirus vaccine antigen. A BSA linked antigen peptide, a PED virus vaccine antigen and a canine coronavirus vaccine antigen were immobilized on ELISA plates in the same manner as above and allowed to be in contact with serum in the same manner as above to measure the serum IgM level in the same manner as above. The results were shown in FIG. 14. As shown in FIG. 14, the serum IgM level significantly increased in the CoV-mMAP administration group through two-step immunization. Form this, it was found that CoV-mMAP, even if it is 4-valent, is effective.

Eight-valent CoV-mMAPs presenting peptides having various modifications were prepared. The peptides used herein were shown in Table 2.

TABLE 2

| | | | SEQ ID NO |
|---|---|---|---|
| No. | Peptide structure | Amino acid sequence | |
| 1 | Original peptide | SAIEDLLFNKV | 8 |
| 2 | D-form amino acids | *SAIEDLLFNKV* | 8 |
| 3 | partially D-form | S̲A̲I̲EDL̲L̲F̲NKV | 8 |
| 4 | partially D-form | *SAIED*LLF*NKV* | 8 |
| 5 | single amino-acid substitution (N→D) | SAIEDLLFDKV | 2 |
| 6 | single amino-acid substitution (A→F) | SFIEDLLFNKV | 1 |

In Table 2, D-form amino acids are shown in italics and underlined and amino acids different from those of No. 1 peptide (SEQ ID NO: 8) are shown in bold letters.

These CoV-mMAPs were administered to mice in accordance with the dosing scheme (regimen) shown in FIG. 9 and serum samples were collected after 2 weeks, 4 weeks, 5 to 6 weeks and 137 days. A PED virus vaccine and a canine coronavirus vaccine were immobilized on ELISA plates and allowed to be in contact with the serum samples to measure serum IgM levels in the same manner as above. The results were shown in FIGS. 15 to 20. As shown in FIGS. 15 to 20, MAPs containing any peptide induced an elevation of virus-specific serum IgM level. From the results, it was found that even if the amino acids to be used in CoV-mMAP are changed to D-form amino acids or if the number of amino acids to be changed falls within the range of one to several, desired induction of IgM was not inhibited. From this, it was clear that CoV-MAP is a vaccine robust against an amino acid change.

The IgM level in the serum sample taken after 137 days was checked. The serum IgM level was obtained as a relative value to serum IgM level before administration of a CoV-mMAP regarded as 1. The results were shown in FIG. 21. As shown in FIG. 21, serum IgM levels specific to the PED virus vaccine and canine coronavirus vaccine increased. From the results, it was found that IgM induced by CoV-mMAP is present and maintained in blood for a long period of 4 months or more.

The effect on immunological memory was then checked. To detect IgM-producing memory cells, mice were immunized with a CoV-mMAP. Using splenocytes on Day 133 after initiation of immunization, IgM production cells against a peptide (SAIEDLLFNKV) were detected by the ELISPOT method. As a negative control, JEV-MAP (8-valent MAP containing a part of the amino acid sequence of E protein of Japanese encephalitis virus) was used. To an ELISPOT plate having peptide-BSA (5 microgram/ml) immobilized thereon, splenocytes were seeded at a density of $5×10^5$ cells/ml, cultured at 37° C. in the presence of 5% $CO_2$ for 22 hours and washed. To the splenocytes, a biotin-labeled anti-IgM antibody (Southern Biotech) was added and a reaction was made at 37° C. for one hour. Thereafter, streptavidin-labeled peroxidase was added to allow spots to emit color in accordance with a routine method. The number of spots was counted by an ELISPOT leader (manufactured by Carl Zeiss KS ELISPOT). The numbers of two wells per individual was averaged. The number of anti-peptide IgM production cells in the CoV-mMAP group was significantly larger than in the JEV-MAP group. From the results, it was found that IgM production cells induced by the CoV-mMAP can be present as memory cells in vivo for a long period of time.

Macrophages express an Fc receptor on the cell surface, bind to IgG against an antigen and take up IgG together with the antigen. The amount of antigen taken up by macrophages is considered to reflect the amount of a virus taken up. When a virus that can infect macrophages is taken up in the macrophages via an antibody, viral infection of the macrophages is promoted due to the presence of the antibody, causing antibody-dependent enhancement of infection (ADE). FLAG-tagged (fusion) recombinant protein was prepared by linking bovine serum albumin (BSA) to a peptide (SAIEDLLFNKV; SEQ ID NO: 8) in a recombinant protein expression system by *Escherichia coli*. The resultant artificial viral peptide, i.e., the peptide-FLAG-BSA (concentration: 5 μg/ml) was mixed with serum (concentration 10%) and the mixture was allowed to react at 37° C. for one hour, added in a culture solution (50,000 cells were seeded) of mouse macrophage cell line P388-D1 cells, cultured at 37° C., in the presence of 5% $CO_2$ for 24 hours to allow the macrophage cells to take up the peptide-FLAG-BSA. The peptide-FLAG-BSA taken up within the cells were subjected to a cell permeabilization treatment with PE (phycoerythrin)—labeled anti-FLAG monoclonal antibody (company: BioLegend), and thereafter, detected by flowcytometry using FACS CantoII (company: Becton Dickinson). Finally, the number of the cells that took up peptide-FLAG-BSA was expressed in percentage relative to the whole viable cells. The results were shown in FIG. 23. As shown in FIG. 23, it was confirmed that the anti-FLAG mouse monoclonal antibody used in place of mouse serum was taken up by almost all cells (99.5%) (positive control). In contrast, the positive cells detected in serum of non-treated healthy mice was only 2.1%. It was found that almost all cells do not take up an IgM bound artificial viral peptide (negative control). In the same conditions as above, the sera of mice immunized with CoV-mMAP (pooled sera on Day 28 and Day 32 before boost vaccination) were used. As a result, the cells that took up the artificial viral peptide was only 3.5%. A big difference was not observed compared to the serum of the healthy mice. The results suggested that if IgM induced by immunization with a CoV-mMAP binds to a virus, the immune complex is not taken up by macrophages.

A CoV-mMAP was administered to mice in accordance with the scheme shown in FIG. 9. Serum samples were taken on Day 25 (before boost vaccination) and Day 60 (after boost vaccination). Thereafter, antigen-specific serum IgG level of each of the serum samples was measured. An antigenic peptide, a canine coronavirus vaccine antigen and a porcine epidemic diarrhea virus antigen were immobilized on ELISA plates as described above, and allowed to be in contact with the serum samples. The serum IgG levels of individual serum samples were measured in the same manner as above. The results were shown in FIG. 24. As shown in FIG. 24, it was found that serum IgG levels against individual antigens increased after boost vaccination.

Similarly, the level of serum IgG bound to each of SARS-CoV-2 spike protein (full length), MERS spike protein and SARS-CoV-2 spike protein (S2 protein) was evaluated. The results were shown in FIG. 25. As shown in FIG. 25, it was found that the level of serum IgG against each of the antigens increased after boost vaccination. Then, analysis was made on IgG subclasses.

As a comparative subject, serum (containing IgG induced by KLH-peptide) of mice immunized with KLH conjugated peptide in combination with alum was used. KLH-peptide induced all IgG subclasses. However, in the serum of mice immunized with CoV-mMAP and boosted with a canine coronavirus antigen, IgG1 alone of the IgG (CoV-mMAP-IgG) subclasses increased in all mouse individuals but IgG2a and IgG2b, which are taken up by macrophages, were rarely detected. From the results, it was found that the immunization with a CoV-mMAP may induce IgG when infected with a virus but does not induce IgG subclasses involved in antibody-dependent enhancement of infection, and thus, have no risk of causing antibody-dependent enhancement of infection, different from vaccines commonly known.

Then, the effect of a CoV-mMAP on infection with a feline infectious peritonitis virus (FIPV) was checked. A group of 4 experimental cats (about 5-months old) previously administered with a CoV-mMAP and a non-treatment group consisting of 4 experimental cats (about 5-months old) were prepared. After onset, the experimental cats were infected with a 100% lethal highly pathogenic coronavirus and feline infectious peritonitis virus (FIPV). The effect of a CoV-mMAP was checked (see, FIG. 27). The CoV-mMAP was intravenously administered on Day 0, 7 and 21 at a dose of 1.5 mg/kg. On Day 7, α-galactosylceramide (0.7 μg/kg) was intravenously administered simultaneously with the CoV-mMAP. Virus exposure was carried out by using a culture solution (10 ml) of CRFK cells at the time when plaque formation of $3\times10^5$ PFU/ml was confirmed. The first administration was via the oral route. To the survival cats, prednisolone was subcutaneously administered at an immunosuppressive dose of 2 mg/kg continuously for 3 days, and thereafter, intraperitoneally administered, as the second administration. The cats developed a symptom excluding a cat developed a symptom by the first administration were intravenously administered with CoV-mMAP and α-galactosylceramide on Day 3 (early administration) and Day 13 to 15 (late administration) similarly to Day 7. The results were shown in FIG. 28. High fever was defined as 39.5° C. or more and the onset of FIP was determined when high fever was confirmed for 3 or more consecutive days. In the CoV-mMAP administration group, Cat No. 5, which developed a symptom because the cat was not administered to with a booster dose of CoV-mMAP, was euthanized (see, cross mark) since high fever did not go down. High fever was improved (went down) in all individuals administered with a booster dose of a CoV-mMAP after onset. In particular, in the CoV-mMAP group, No. 7 cat early received a booster dose (administered 3 days after onset) reduced in body temperature up to normal temperature (temperature before exposure to a virus) and was completely cured. FIPV is known to be the most pathogenic coronavirus. Affected cats are nearly 100% fatal. The multiple antigen peptide of the present invention prevents onset of infection with FIPV and produces a therapeutic effect on the infection. In this respect, the multiple antigen peptide of the present invention has an extremely great technical significance. In the CoV-mMAP administration group, No. 3 cat lately received a booster dose was euthanized because other symptoms such as ascites did not subside although the fever was reduced to a low grade. In the non-treatment group, No. 4 and No. 6 cats were euthanized because both once reduced in body temperature to a low grade by administration of CoV-mMAP but again had high fever. The results are summarized in Table 3.

TABLE 3

| | | CoV-mMAP group | | | Non-treatment group | |
|---|---|---|---|---|---|---|
| Onset | | 3/4 | | | 2/4 | |
| Treated after onset | Not treated | Early administration of CoV-mMAP (Day 3 after onset) | Late administration of CoV-mMAP (Day 15 after onset) | Early administration of CoV-mMAP (Day 3 after onset) | Late administration of CoV-mMAP (Day 13 after onset) | |
| Number of individuals | No. 5 | No. 7 | No. 3 | No. 4 | No. 6 | |
| Course of disease | Symptom progressed with high fever, euthanized | Normal temperature, no symptoms, recovered | Reduced to normal temperature but symptom progressed, euthanized | Body temperature is reduced to a low-grade but again increased, symptom progressed, euthanized | Body temperature is reduced to a low-grade but again increased, symptom progressed, euthanized | |
| Individuals recovered/individuals onset | | 1/3 | | | 0/2 | |
| Effect | Onset but recovered with early booster shot | | | Fail to recover | | |

Symptoms of individuals

DISCUSSION

SARS-CoV-2 has a problem in that it infects not only respiratory tract mucosal cells but also macrophages, causing systemic inflammation due to cytokine storm and leading to multiple organ failure. This can be explained by elevation of IgG subclasses (IgG2 in mice and IgG1 in humans) having high affinity for IgG receptors on macrophages. (FIG. 1). Antibody-dependent enhancement of infection (ADE) is a phenomenon commonly observed in viruses infecting macrophages, such as Dengue virus, Zika virus and Ebola virus, and an inevitable phenomenon for conventional inactivated vaccines using viral proteins. This is because a viral protein stimulates immune response via T cells to produce an antibody, with the result that IgG having a high affinity for (T cell-dependent) IgG receptor is induced to cause ADE. ADE can be avoided by inducing an antibody that does not bind to an IgG receptor, in other words, directly stimulating B cells without T cell intervention (T cell-independent) (Saravanan, P., et. al., Acta Virol., (48) 39-45, 2004). Technically, a vaccine produced by a multiple antigen peptide (MAP) corresponds to a specific means.

FIG. 2 shows the structure of a multiple antigen peptide presenting 4 antigens (more specifically, 4-valent) and that the multiple antigen peptide directly stimulates marginal zone B cells and B1B cells without helper T cell intervention to produce IgG subclasses (IgG1 and IgG3 in the case of a mouse) not binding to IgM and IgG receptors. It is considered that the multiple antigen peptide directly stimulates marginal zone B cells and B1B cells, and allows B cell receptors expressed on the surface to form a cluster, which stimulates B cells to produce an antigen-specific antibody.

WO2018/084247A discloses that a 4-valent multiple antigen peptide (MAP-4) and 8-valent multiple antigen peptide (MAP-8) containing a partial peptide of influenza-virus hemagglutinin as an antigen were administered to mice and that IgG and IgM of the mice increased after administration.

When the amount of an antibody in serum was measured for each of the IgG subtypes, IgG1 and IgG3, which are subtypes which does not bind to an IgG receptor, were induced but IgG 2a, which binds to an IgG receptor, was not induced. This result suggests that, when the immune system of an animal body was stimulated with MAP, marginal zone B cells and B1B cells are directly stimulated to induce only an antibody which does not bind to an IgG receptor, and that production of an antibody is induced in a T cell-independent manner. To stimulate marginal zone B cells and B1B cells, it has been clarified that the number of antigenic peptides to be linked to a multiple antigen peptide is enough to be 4.

The result shows that B cells stimulated by MAP are marginal zone B cells and B1B cells present in mucous membrane and serosal membrane and not the follicle B cells producing an antibody in T-cell dependent manner. The result is consistent with the finding that the antibody produced by these B cells is principally an antibody which does not bind to an IgG receptor (IgM, and IgG3 in the case of mice) or an IgG subclass (IgG 1 in the case of mice) having a low binding ability (Bennett, K M., et. al., BMC Biotechnol, (15)71, 2015) (FIG. 2).

IgM stimulated and produced in a T-cell dependent manner disappears in about 7 to 10 days whereas IgM produced in a T cell-independent manner is present in blood for a long period of time (about 90 days in mice) (Dintzis, H M, et. al., Proc. Natl. Acad. Sci. USA, (73) 3671-5, 1974). Thus, long-term viral protection can be expected to some extent.

According to the above results, ADE can be avoided by inducing an antibody which does not bind to an IgG receptor, in other words, directly stimulating B cells without T cell intervention (T cell-independent) (Saravanan, P., et. al., Acta Virol., (48) 39-45, 2004). Technically, ADE can be avoided by a vaccine produced by a multiple antigen peptide.

The peptide of the present invention has an amino acid sequence conserved in a wide variety of coronaviruses belonging to the family coronavirus. Therefore, the peptide of the present invention can produce an antibody effective for the whole coronaviruses. The amino acid sequence conserved in a wide variety of coronaviruses suggests that the amino acid sequence has been conserved without being affected by mutations repeatedly occurred, in other words, the multiple antigen peptide of the present invention is mutation-compatible MAP (mMAP) and effective for coronaviruses that may appear in future.

In the present invention, in-vivo production (induction) of an antibody against a coronavirus using a short peptide consisting of 11 amino acids was achieved. Since the 11 amino acids constituting the short peptide correspond to those of the amino acid sequence conserved in a wide variety of coronaviruses, the finding that the short peptide is sufficient to produce an antibody against a coronavirus suggests the possibility of producing a vaccine against all types of coronaviruses. In this sense, the finding is meaningful. Actually, the multiple antigen peptide of the present invention promotes production of effective antibodies against a porcine coronavirus and a canine coronavirus, and has a significance in view of zoonotic infectious diseases.

The MAP chemically synthesized can be quickly produced in a large scale different from vaccines using a recombinant protein and a vector requiring a culture step. The method according to the present invention is considered as the most appropriate technique for producing vaccines against a pandemic infection disease, for example, caused by COVID-19, and requiring an urgent countermeasure.

LISTING OF SEQUENCES

SEQ ID NO: 1: the amino acid sequence of a partial peptide of spick protein of SARS-CoV-2

SEQ ID NO: 2: the amino acid sequence of a partial peptide of spick protein of FIPV having an amino acid sequence corresponding to the amino acid sequence of SEQ ID NO: 1

SEQ ID NO: 3: the amino acid sequence of a partial peptide of spick protein of SARS-CoV-2 containing an amino acid sequence around the amino acid sequence of SEQ ID NO: 1

SEQ ID NO: 4: the amino acid sequence of an antigen peptide (a partial peptide of a spike protein of SARS-CoV-2) integrated in β-sheet peptide sequence SEQ ID NO: 5: the amino acid sequence of a partial peptide of influenza-virus hemagglutinin SEQ ID NO: 6: the amino acid sequence of a partial peptide of a spike protein of PEDV having the amino acid sequence corresponding to the amino acid sequence of SEQ ID NO: 1.

SEQ ID NO: 7: the sequence of an antigenic peptide
SEQ ID NO: 8: the sequence of an antigenic peptide

The invention claimed is:

1. A multiple antigen peptide comprising four to eight peptides, each peptide consisting of an amino acid sequence of a coronavirus spike protein consisting of 11 consecutive amino acids set forth in SEQ ID NO: 7.

2. The multiple antigen peptide according to claim 1, wherein the amino acid sequence set forth in SEQ ID NO: 7 is SEQ ID NO: 1, 2, 6, or 8.

3. The multiple antigen peptide according to claim 1, comprising a dendritic polymer backbone and a peptide, wherein the peptide is linked to a tail end of the dendritic polymer backbone.

4. The multiple antigen peptide according to claim 3, wherein the dendritic polymer backbone and the peptide are linked via a linker to each other.

5. The multiple antigen peptide according to claim 3, wherein, in the dendritic polymer backbone, to each of 2 amino groups of a lysine residue, a lysine residue forming a first-generation branch is bound via a peptide bond; and to each of 4 amino groups of the lysine residues forming a first-generation branch thus formed, a peptide is linked with or without a linker.

6. The multiple antigen peptide according to claim 3, wherein, in the dendritic polymer backbone, to each of 2 amino groups of a lysine residue, a lysine residue forming a first-generation branch is bound via a peptide bond; to each of 4 amino groups of the lysine residue forming the first-generation branch, a lysine reside forming a second-generation branch is bound via a peptide bond; and to each of 5 or more, 6 or more, 7 or more or 8 or more amino groups of the lysine residues forming a second-generation branch thus formed, a peptide is linked with or without a linker.

7. The multiple antigen peptide according to claim 1, having the following formula (VI):

(VI)

wherein R represents-linker-peptide or -peptide, the peptide is the peptide according to any one of claims 1 to 5; R² represents a hydrogen atom, an OH group, a substituted or unsubstituted lower alkyl group, an amino group, an amino acid, a halogen atom or a peptide; and the amino acid is linked to the above molecule via an amide bond.

8. A vaccine against a coronavirus, comprising the multiple antigen peptide according to claim 1.

9. The vaccine according to claim 8, comprising no adjuvants.

10. The vaccine according to claim 8, wherein the coronavirus is SARS-CoV-2 or a mutant virus thereof.

11. The vaccine according to claim 8, wherein the coronavirus is one or more coronaviruses selected from porcine epidemic diarrhea virus (PED), canine coronavirus and feline infectious peritonitis virus (FIPV).

12. A pharmaceutical composition comprising the multiple antigen peptide according to claim 1.

13. A method for administering a peptide to a subject, comprising administering an effective amount of the pharmaceutical composition according to claim 12 to the subject.

14. A method comprising administering an effective amount of the pharmaceutical composition according to claim 12 to a subject, wherein the method
  (a) activates immunity against a coronavirus in the subject;
  (b) induces antigen-specific immunity against a coronavirus in the subject;
  (c) induces an antigen-specific IgM antibody against a coronavirus in the subject;
  (d) induces formation of immunological memory against a corona virus in the subject; and/or
  (e) prevents and/or treats an infection with a coronavirus in the subject.

15. The multiple antigen peptide according to claim 1, wherein at least one of the peptides consists of the amino acid sequence set forth in SEQ ID NO: 1.

16. The multiple antigen peptide according to claim 1, wherein at least one of the peptides consists of the amino acid sequence set forth in SEQ ID NO: 6.

17. The multiple antigen peptide according to claim 1, wherein at least one of the peptides consists of the amino acid sequence set forth in SEQ ID NO: 8.

* * * * *